(12) United States Patent
Bozhko et al.

(10) Patent No.: US 12,320,750 B2
(45) Date of Patent: Jun. 3, 2025

(54) TESTING OF A LUMINESCENCE IMAGING APPARATUS WITH INCLINED CONTAINERS OF LUMINESCENCE SUBSTANCE

(71) Applicant: SurgVision GmbH, Munich (DE)

(72) Inventors: Dmitry Bozhko, Munich (DE); Maximilian Koch, Munich (DE); Adrian Taruttis, Munich (DE); Christian Aichinger, Munich (DE); Jurek Nordmeyer-Massner, Augsburg (DE)

(73) Assignee: SURGVISION GMBH, Munich (DE)

( * ) Notice: Subject to any disclaimer, the term of this patent is extended or adjusted under 35 U.S.C. 154(b) by 317 days.

(21) Appl. No.: 17/779,516

(22) PCT Filed: Nov. 19, 2020

(86) PCT No.: PCT/EP2020/082671
§ 371 (c)(1),
(2) Date: May 24, 2022

(87) PCT Pub. No.: WO2021/104987
PCT Pub. Date: Jun. 3, 2021

(65) Prior Publication Data
US 2023/0003650 A1 Jan. 5, 2023

(30) Foreign Application Priority Data
Nov. 25, 2019 (EP) .................................... 19211282

(51) Int. Cl.
*G01N 21/64* (2006.01)
*A61B 5/00* (2006.01)

(52) U.S. Cl.
CPC ........ *G01N 21/6456* (2013.01); *A61B 5/0071* (2013.01); *G01N 2201/12* (2013.01)

(58) Field of Classification Search
CPC ............... G01N 21/6456; G01N 21/64; G01N 2201/12; A61B 5/0071; A61B 2560/0223; G01J 3/027; G01J 3/0291; G01J 3/443
See application file for complete search history.

(56) References Cited

U.S. PATENT DOCUMENTS

| 8,373,860 B2 * | 2/2013 | Kiesel .................. G01N 21/255 356/417 |
| 2003/0146663 A1 | 8/2003 | Nelson et al. |

(Continued)

FOREIGN PATENT DOCUMENTS

| EP | 3460457 A1 | 3/2019 |
| JP | 2015125028 A | 7/2015 |

OTHER PUBLICATIONS

European Office Action for Application No. 20 823 735.4 dated Jan. 22, 2024.

(Continued)

*Primary Examiner* — Suman K Nath
(74) *Attorney, Agent, or Firm* — Bryan A. Santarelli; FisherBroyles, LLP

(57) ABSTRACT

A solution is proposed for testing a luminescence imaging apparatus (105). A corresponding testing device (110) comprises one or more seats (320) and one or more containers (325), each filled with a liquid comprising at least one luminescence substance and accommodated in a corresponding seat (320); the seats (320) have corresponding windows (330) for imaging the luminescence substance of the containers (325) accommodated therein. The seats (320) are slanted with respect to a resting surface (310) of the testing device (110). A holder (305) for use in the testing device (100) is further provided. A luminescence imaging apparatus (105) for use with the testing device (110) is also proposed. Moreover, a system (100) comprising a lumines- (Continued)

cence imaging apparatus (105) and this testing device (110) is proposed.

26 Claims, 8 Drawing Sheets

(56) References Cited

U.S. PATENT DOCUMENTS

| | | |
|---|---|---|
| 2009/0056639 A1 | 3/2009 | Ragatz et al. |
| 2010/0020303 A1* | 1/2010 | Unno .................. G03F 7/70566 355/71 |
| 2012/0046203 A1 | 2/2012 | Walsh et al. |
| 2012/0179383 A1 | 7/2012 | Yeo et al. |

OTHER PUBLICATIONS

European Office Action for Application No. 20 823 734.7 dated Jun. 1, 2023.
Hoogstins et al., "Setting Standards for Reporting and Quantification in Fluorescence-Guided Surgery", May 29, 2018. Molecular Imaging and Biology, vol. 21, No. 1, pp. 11 through 18.
International Searching Authority, "International Search Report and Written Opinion from PCT Application No. PCT/EP2020/082671, dated Feb. 9, 2021", pp. 1 through 19, Published in: EP.
Notification of First Office Action dispatched Mar. 31, 2025 for JP Application No. 202080075308.6, a counterpart application of U.S. Appl. No. 17/779,516, 24 pgs.

* cited by examiner

TESTING OF A LUMINESCENCE IMAGING APPARATUS WITH INCLINED CONTAINERS OF LUMINESCENCE SUBSTANCE

This application claims priority to International Patent Application No. PCT/EP2020/082671 filed on Nov. 19, 2020, which claims priority to European Patent Application No. 19211282.9 filed on Nov. 25, 2019, which applications are incorporated by reference herein.

TECHNICAL FIELD

The present disclosure relates to imaging applications. More specifically, this disclosure relates to luminescence imaging.

BACKGROUND ART

The background of the present disclosure is hereinafter introduced with the discussion of techniques relating to its context. However, even when this discussion refers to documents, acts, artifacts and the like, it does not suggest or represent that the discussed techniques are part of the prior art or are common general knowledge in the field relevant to the present disclosure.

Imaging generally relates to a number of techniques that allow acquiring images of objects (typically, not visible directly) in a substantially non-invasive manner. For example, imaging techniques are routinely exploited in equipment for medical applications to inspect (inner) body-parts of patients for diagnostic, therapeutic and/or surgical purposes.

A specific imaging technique increasingly considered is luminescence imaging, and especially fluorescence imaging. Luminescence imaging is based on a luminescence phenomenon, consisting of the emission of light by luminescence substances when subject to any excitation different from heating; particularly, a fluorescence phenomenon occurs in fluorescence substances (called fluorophores), which emit light when they are illuminated (with an intensity depending on an amount of the fluorophores that are illuminated). For example, this phenomenon is leveraged in medical applications by administering fluorescence agents to the patients, and especially targeted fluorescence agents adapted to reaching a specific molecule of a desired target and then to remaining immobilized thereon (for example, thanks to a specific interaction with tumoral tissues).

For this purpose, (fluorescence) imaging apparatuses are used; the imaging apparatuses allow illuminating each object to be imaged (with an excitation light suitable to excite the fluorophores) and to acquire corresponding (fluorescence) images representing the fluorophores present in the object, often together with (photograph) images simply representing the object; particularly, in medical applications the fluorescence images represent the fluorescent agent immobilized on the corresponding target and the photograph images represent the body-parts under analysis.

The imaging apparatuses should be tested to verify their performance. This is especially important in medical applications, wherein the performance of the imagining apparatuses affects corresponding diagnostic, therapeutic and/or surgical results.

The test of the imaging apparatuses may be carried out with specific metering instruments. However, this does not allow verifying an illumination unit and an acquisition unit of the imaging apparatuses simultaneously. Another possibility is of using a curable polyurethane matrix or a composite phantom embedding quantum dots (small particles manufactured in a semiconductor process) in different concentrations, for example, as described in U.S. Pat. No. 9,167,240. However, the quantum dots exhibit a very high absorption of visible light (particularly, far higher than the one of the fluorescence agents typically used in medical applications), so that they may be used to verify the performance of the imaging apparatuses only in environments with controlled illumination.

In order to test the imaging apparatuses in a close simulation of their actual usage, it is instead possible to use samples of the same fluorophores to be imaged, i.e., the fluorescence agents in medical applications. Several testing devices are available for this purpose. For example, it is possible to use well plates (commonly used in laboratories for other purposes), loosely arranged tubes or capillary tubes being filled with different concentrations of the fluorescence agent. However, these testing devices require manual interventions (for example, on-site preparations and selections of regions of interest in the images), which are inconvenient and error-prone.

Moreover, "Setting Standard for Reporting and Quantification in Fluorescence-Guided Surgery" by Hoogstings et al., Mol Imaging Biol (2019) 21:11-18 proposes the use of a testing device by SurgVision called CalibrationDisk (trademarks thereof). This testing device is formed by an upper disk (holding eight tubes filled with different concentration of a fluorescence agent) and a base on which the upper disk may rotate.

US-A-2012/179383 discloses a disc including a calibration unit for calibrating a measurement unit of a biomaterial test device. EP-A-3460457 discloses a calibration reference body accommodating different fluorescence bodies that emit fluorescence in a same wavelength band when irradiated with excitation light in different wavelength bands (in a different amount when the excitation lights are equal to each other).

SUMMARY

A simplified summary of the present disclosure is herein presented in order to provide a basic understanding thereof, however, the sole purpose of this summary is to introduce some concepts of the disclosure in a simplified form as a prelude to its following more detailed description, and it is not to be interpreted as an identification of its key elements nor as a delineation of its scope.

In general terms, the present disclosure is based on the idea of inclining containers of luminescence substance.

Particularly, an aspect provides a testing device for testing a luminescence imaging apparatus. The testing device comprises one or more seats and one or more containers, each filled with a liquid comprising at least one luminescence substance and accommodated in a corresponding seat; the seats have corresponding windows for imaging the luminescence substance of the containers accommodated therein. The seats are slanted with respect to a resting surface of the testing device.

A further aspect provides a holder for use in the testing device.

A further aspect provides a luminescence imaging apparatus for use with the testing device.

A further aspect provides a luminescence imaging system comprising a luminescence imaging apparatus and the testing device.

More specifically, one or more aspects of the present disclosure are set out in the independent claims and advantageous features thereof are set out in the dependent claims, with the wording of all the claims that is herein incorporated verbatim by reference (with any advantageous feature provided with reference to any specific aspect that applies mutatis mutandis to every other aspect).

BRIEF DESCRIPTION OF THE DRAWINGS

The solution of the present disclosure, as well as further features and the advantages thereof, will be best understood with reference to the following detailed description thereof, given purely by way of a non-restrictive indication, to be read in conjunction with the accompanying drawings (wherein, for the sake of simplicity, corresponding elements are denoted with equal or similar references and their explanation is not repeated, and the name of each entity is generally used to denote both its type and its attributes, such as value, content and representation). Particularly.

DETAILED DESCRIPTION

Figure 1:
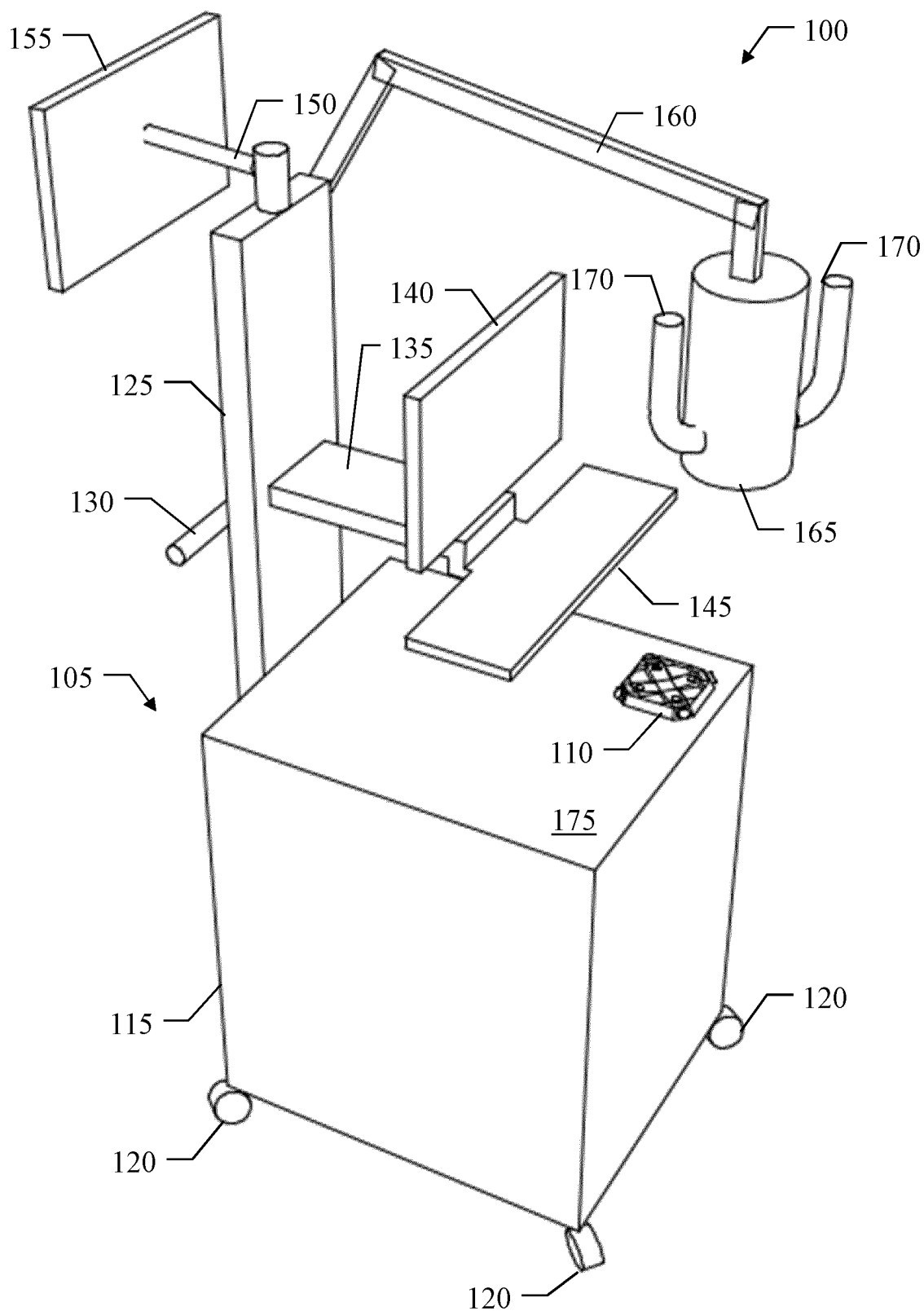
FIG. 1 shows a pictorial representation of a fluorescence imaging system according to an embodiment of the present disclosure.

With reference in particular to FIG. 1, a pictorial representation is shown of a (fluorescence) imaging system 100 according to an embodiment of the present disclosure. The imaging system 100 comprises a (fluorescence) imaging apparatus 105 known per se and a testing device 110 according to an embodiment of the present disclosure.

The imaging apparatus 105 is used in medical applications to inspect body-parts of patients (not shown in the figure), for example, for diagnostic, therapeutic and/or surgical purposes. The imaging apparatus 105 comprises the following components. A trolley 115 houses a supply unit and a control unit (not visible in the figure) for supplying and controlling, respectively, the imaging apparatus 105. Four casters 120 (only three visible in the figure) are arranged at corresponding lower corners of the trolley 115 to facilitate moving the imaging apparatus 105 (with a foot brake, not visible in the figure, that is provided for securing the imaging apparatus 105 in position). A pillar 125 extends upwards from a back surface of the trolley 115. The pillar 125 has a handlebar 130 for moving the imaging apparatus 105 by an operator thereof. A cantilever 135 projects from the pillar 125, above the trolley 115. A primary monitor 140 (for displaying images to the operator) and a keyboard with a pointing device such as a mouse or a trackball 145 (for entering information/commands by the operator) are mounted on the cantilever 135. A pivoting arm 150 is mounted on top of the pillar 125 (above the cantilever 135). A secondary monitor 155 (for displaying images to a doctor, such as a surgeon) is mounted on the pivoting arm 150 (so as to allow turning it in either directions). An articulated arm 160 is mounted on top of the pillar 125 as well (next to the pivoting arm 150). An imaging head 165 (for imaging a scene within its field of view, and particularly the body-parts under analysis) is suspended from the articulated arm 160. The imaging head 165 is provided with two handlebars 170 for positioning it by the operator.

The testing device 110 is used to test the imaging apparatus 105 for verifying its performance. For example, the test is aimed at calibrating the imaging apparatus 105, at ensuring that the imaging apparatus 105 operates correctly, at monitoring operation of the imaging apparatus 105 over time and/or at comparing the imaging apparatus 105 with different ones. For this purpose, the testing device 110 is rested on a supporting surface 175, so as to be positioned within the field of view of the imaging head 165; particularly, in the exemplary implementation shown in the figure the supporting surface 175 is defined by a top surface of the trolley 115.

Figure 2:
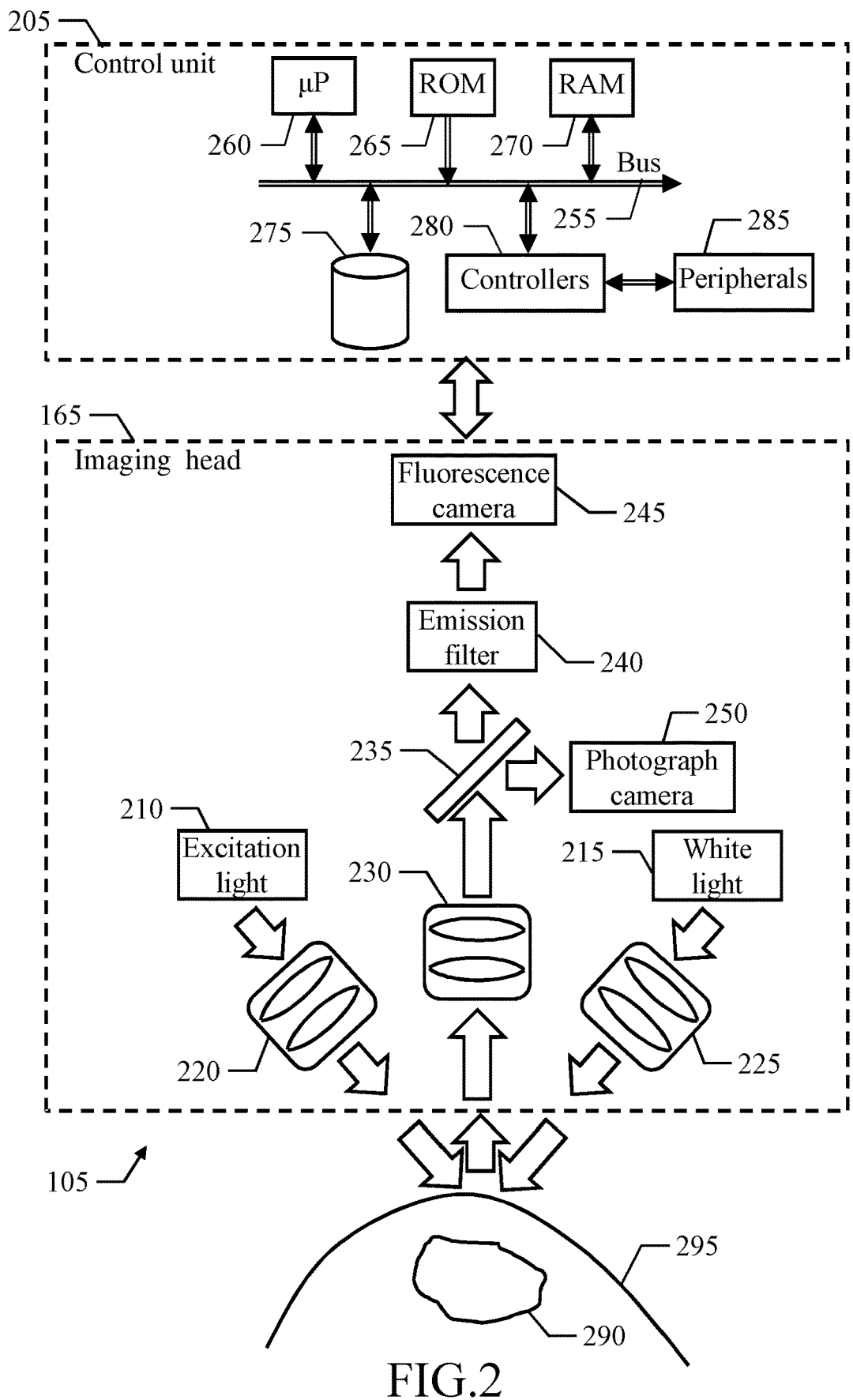
FIG. 2 shows a schematic block diagram of a fluorescence imaging apparatus that may be used to practice the solution according to an embodiment of the present disclosure.

With reference now to FIG. 2, a schematic block diagram is shown of the imaging apparatus 105 that may be used to practice the solution according to an embodiment of the present disclosure.

Particularly, the figure shows a functional structure of the imaging head 165 and of the control unit, denoted with the reference 205.

Starting from the imaging head 165, it has an illumination unit and an acquisition unit for illuminating the scene in its field of view and for acquiring images thereof, respectively.

The illumination unit comprises the following components. An excitation light source 210 and a white light source 215 generate an excitation light and a white light, respectively. The excitation light has wavelength and energy suitable to excite the fluorophores of the fluorescence agent (such as of Near Infra-Red, or NIR, type), whereas the white light appears substantially colorless to the human eye (such as containing all the wavelengths of the spectrum that is visible to the human eye at equal intensity). Corresponding delivery optics 220 and delivery optics 225 deliver the excitation light and the white light, respectively, to the (same) field of view of the imaging head 165.

The acquisition unit comprises the following components. Collection optics 230 collect light from the field of view (in an epi-illumination geometry). The collected light comprises fluorescence light that is emitted by any fluorophores present in the field of view. Indeed, the fluorophores pass to an excited (electronic) state when they absorb the excitation light; the excited state is unstable, so that the fluorophores very shortly decay therefrom to a ground (electronic) state, thereby emitting the fluorescence light (at a characteristic wavelength, longer than the one of the excitation light because of energy dissipated as heat in the excited state) with an intensity depending on an amount of the fluorophores that are illuminated. Moreover, the collected light comprises visible light (in the visible spectrum) that is reflected by any object present in the field of view (illuminated by the white light). A beam-splitter 235 splits the collected light into two channels. For example, the beam-splitter 235 is a dichroic mirror transmitting and reflecting the collected light at wavelengths above and below, respectively, a threshold wavelength between a spectrum of the fluorescence light and a spectrum of the visible light. In one of the channels of the beam-splitter 235 with the (portion of the) collected light in the spectrum of the fluorescence light (such as the transmitted one), an emission filter 240 receives the fluorescence light and filters it to remove any excitation light (which might be reflected by objects in the field of view) and any ambient lights (which might be generated by background/inherent fluorescence). A fluorescence camera 245 receives the fluorescence light from the emission filter 240 and generates a corresponding fluorescence (digital) image representing the distribution of the fluorophores in the field of view. In the other one of the channels of the beam-splitter 235 with the (portion of the) collected light in the spectrum of the visible light (such as the reflected one), a photograph camera 250 receives the visible light and generates a corresponding photograph (digital) image representing a visualization of the objects in the field of view.

Moving to the control unit 205, it comprises several units that are connected among them through a bus structure 255. Particularly, one or more microprocessors (μP) 260 provide processing and orchestration functionalities of the control unit 205. A non-volatile memory (ROM) 265 stores basic code for a bootstrap of the control unit 205 and a volatile memory (RAM) 270 is used as a working memory by the microprocessors 260. The control unit 205 is provided with a mass-memory 275 for storing programs and data (for example, a Solid-State-Disk, or SSD). Moreover, the control unit 205 comprises a number of controllers 280 for peripherals, or Input/Output (I/O) units; particularly, the controllers 280 control the excitation light source 210, the white light source 215, the fluorescence camera 245 and the photograph camera 250 of the imaging head 165; moreover, the controllers 280 control further peripherals, denoted as a whole with the reference 285, such as the primary monitor, the keyboard, the pointing device, the secondary monitor, a drive for reading/writing removable storage units (such as of USB type) and a network interface card (NIC) for connecting to a communication network (such as a LAN and then the Internet).

In operation, the imaging head 165 is used to image a body-part 290 of a patient 295 during an imaging process thereof (for example, a diagnostic analysis, a therapeutic treatment or a surgical intervention). For this purpose, a fluorescence agent is administered to the patient 295 (for example, intravenously or locally). The fluorescence agent is a target-specific fluorescence agent that is adapted to attaching to a specific (biological) target by means of a specific interaction therewith (such as tumoral tissues, nerves, blood-vessels, lymph-nodes, lymph-vessels and so on). The fluorescence agent is administered to the patient 295 in advance (such as 24-72 hours before the imaging process), so as to allow the fluorescence agent to circulate within a vascular system of the patient 295 until reaching the body-part 290 and binding to the desired target. During the imaging process, the imaging head 165 is positioned to have the body-part 290 within its field of view. At this point, the body-part 290 is illuminated with both the excitation light and the white light; fluorescence images (representing the distribution of the fluorescence agent, and then of its target, in the body-part 290) and photograph images (representing the visualization of the body-part 290) are acquired in succession. The fluorescence/photograph images are then displayed onto the primary/secondary monitors of the imaging apparatus, generally overlaid to each other into corresponding combined images (representing the target being contextualized on an anatomical structure of the body-part 290).

Figure 3:
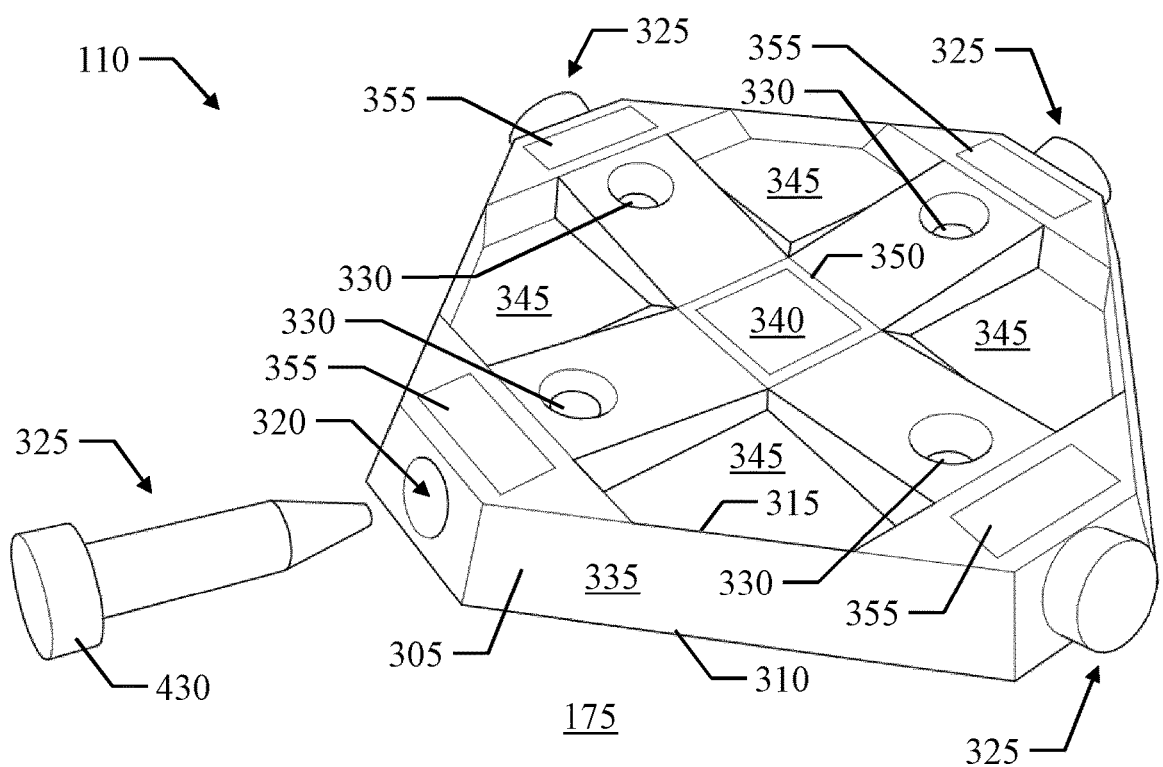
FIG. 3-FIG. 4 show different views of a testing device according to an embodiment of the present disclosure.
Figure 4:
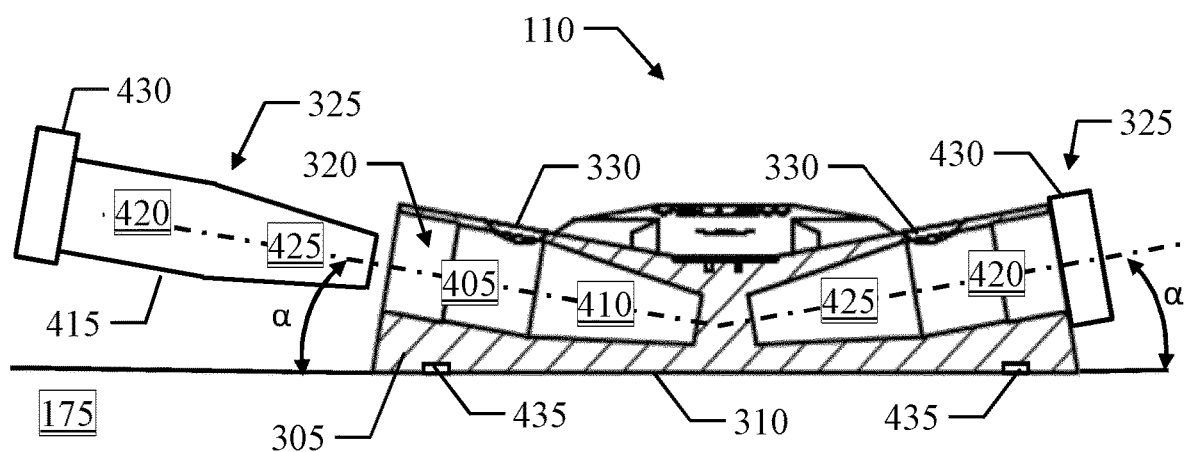

With reference now to FIG. 3-FIG. 4, different views are shown of the testing device 110 according to an embodiment of the present disclosure.

Starting from FIG. 3, it shows a perspective view of the testing device 110. The testing device 110 has a main body (for example, of plastic material) defining a holder 305. The holder 305 has a (bottom) resting surface 310 for resting the testing device 110 on any supporting surface, for example, the supporting surface 175 of the trolley of the imaging apparatus, not shown in the figure; the holder 305 has a (top) imaging surface 315 opposite the resting surface 310 for imaging the testing device 110. One or more seats 320 (four in this specific implementation, only one visible in the figure) are provided in the holder 305. The seats 320 are configured to accommodate corresponding containers 325 (one shown outside the seat 320 and three shown inside the seats 320 in the figure). Each container 325 is filled with a liquid containing a fluorescence agent (or more); for example, the containers 325 are of different types each defined by the corresponding fluorescence agent and/or its concentration. The testing device 110 may be either in a basic version or in a complete version. In the basic version, the testing device 110 is provided without the containers 325 (to be acquired separately and then inserted into the seats 320 in a removable way). In the complete version, instead, the testing device 110 is provided with the containers 325 already inserted in the seats 320 (either in a removable way or in a non-removable way). Windows 330 corresponding to the seats 320 are opened in the imaging surface 315. Each window 330 exposes part of the corresponding seat 320; therefore, each window 330 also exposes a corresponding part of the container 325 accommodated in the seat 320 so as to allow imaging its fluorescence agent. For this purpose, at least the part of the container 325 exposed through the window 330 is transparent to both the excitation light and the fluorescence light (i.e., it is capable of allowing the excitation/fluorescence light to pass through it substantially without being excessively diffused, such as with a ratio, between the radiant power of a beam of excitation/fluorescence light exiting the container 325 in a direction defined by a corresponding angle of refraction and the radiant power of a beam of excitation/fluorescence light entering the same container 325 being slanted with respect to its surface, higher than 80%, preferably higher than 85% and even more preferably higher than 90%, such as between 95% and 100%).

Moving to FIG. 4, it shows a cross-section view of the same testing device 110; particularly, the cross-section view is in a (vertical) symmetry plane, perpendicular to the resting surface 310, of two opposed seats 320 (one with the container 325 outside it and the other one with the container 325 inside it in the figure). In the solution according to an embodiment of the present disclosure, the seats 320 are inclined with respect to the resting surface 310 (i.e., a longitudinal axis thereof is not parallel to the resting surface 310). Because of the inclination of the seats 320, the containers 325 accommodated therein are inclined with respect to the resting surface 315 as well. Therefore, when the testing device 110 rests on the supporting surface 175 (substantially horizontally), the containers 325 are not horizontal. Moreover, each window 330 is spaced apart from a distal (top) end of the corresponding seat 320, more distant from the resting surface 310 than another proximal (bottom) end thereof.

As a result, any impurities that may be present in the containers 325 (such as air bubbles and small floating particles) naturally flow upwards and accumulate there, away from the corresponding windows 330. This ensures that the parts of the containers 325 that are imaged through the windows 330 are substantially free of impurities.

Moreover, the containers 325 may not be filled completely; in this case as well, air remaining in the containers 325 flows upwards and accumulate there, away from the corresponding windows 330. This ensures that the parts of the containers 325 that are imaged through the windows 330 are substantially full of the fluorescence agent.

All of the above significantly increases a quality of the imaging of the containers 325, which reflects in an improved accuracy of any tests of the imaging apparatus performed with the testing device 110.

The specific implementation of the testing device 110 shown in the figure provides additional advantages.

Particularly, the longitudinal axes of the seats 320 form an incline angle α of 5-30°, preferably 7-20° and still more preferably 9-15°, such as 10°, with the supporting surface 175. These values of the incline angle α provide a fast flowing upwards of the impurities and the air (for example, so as to allow using containers 325 even filled by 70-90% only); at the same time, they do not adversely affect the imaging of the containers 325.

A distance of the windows 330 (i.e., their upper borders) from the distal end of the corresponding seats 320 is 10-50%, preferably 20-40% and still more preferably 25-35%, such as 30% of a length of the seats 320 (along their longitudinal axis). These values of the distance ensure that any impurities and/or air in the containers 325 are never imagined through the windows 330 in most practical situations.

Each seat 320 has an external portion 405 with a constant section (for example, with a cylindrical shape) and an internal portion 410 with a section decreasing moving inwards the holder 305 (for example, with a frusto-conical shape). The corresponding window 330 exposes at least part of the external portion 405 of the seat 320. The containers 325 accommodated in the seats 320 have a matching shape. For example, the containers 325 are commercial off-the-shelf vials of 1.5 ml. Each vial 325 comprises a (transparent) elongated bottle 415 (such as of plastic material) containing the liquid with the fluorescence agent. Accordingly, the bottle 415 has a top portion 420 (proximal to an opening thereof) with a constant section (for example, with a cylindrical shape) and a bottom portion 425 (distal from the opening) with a section decreasing moving away from the opening (for example, with a frusto-conical shape). Each vial 325 further comprises a cap 430 closing the bottle 415 (for example, of screw-on type). Therefore, the windows 330 expose at least part of the top portions 420 of the containers 325 (and particularly their lowest part). In this way, the containers 325 are imaged where they are substantially flat.

One or more magnetic elements 435 (two in this specific implementation) are embedded in the holder 305, close to the resting surface 310. When the supporting surface 175 is of ferromagnetic material (such as iron), the magnetic elements 435 generate an attraction force that maintains the testing device 110 (rested thereon) fixed in position.

Returning to the FIG. 3, the holder 305 has a shape (in plant view) having point symmetry; in this specific implementation, the shape is octagonal, with four long edges and four short edges alternated to each other. The holder 305 then has a lateral surface 335 (extending between the resting surface 310 and the imaging surface 315) with four big faces and four small faces alternated to each other (corresponding to the long edges and the short edges, respectively). The seats 320 comprise corresponding blind holes, which extend inwards from the lateral surface 335, and more specifically from the small faces thereof. The windows 330 comprise corresponding through-holes, which reach the seats 320 from the imaging surface 315. As a result, by placing a center of illumination of the imaging head defining its optical axis (not show in the figure) at a central point of the holder 305, it is possible to have a same illumination of all the containers 325 through the windows 330 (symmetric thereto).

The windows 330 are opened in portions of the imaging surface 315 that are inclined with respect to the resting surface 310. For example, the portions of the imaging surface 315 around the windows 330 are oriented inwards the holder 305 (downwards) moving towards its central point, so as to form an angle with the resting surface 310 of 5-15° (such as 10°). This reduces a reflection of the imaging surface 315 (at least close to the windows 330) when the testing device 110 is illuminated from above.

The windows 330 have corresponding edges at the imaging surface 315 which are chamfered. For example, the edges are chamfered to form an angle of 40-50° (such as of 45°) with the imaging surface 315. This reduces any shadowing of the windows 330 when the testing device 110 is illuminated from above.

The holder 305 has one or more markers 340,345 arranged on the imaging surface 315 (for example, formed by corresponding labels stitched thereon), which are machine-readable optically (for example, QR codes). The markers 340,345 operate as positional markers for determining a position (i.e., location and orientation) of the testing device 110. Particularly, in this specific implementation a (central) marker 340 is arranged at the central point of the holder 305 and four (window) markers 345 are arranged in correspondence to the windows 330 (for example, alternated to each other).

One or more of the markers 340,345 may further operate as informative markers encoding (device) information of the testing device 110. For example, one marker 340,345 or multiple makers 340,345 in combination encode a (unique) device identifier of the testing device 110 (for example, with the device identifier encoded in the marker 340). The device identifier allows tracking a usage of the testing device 110. The testing device 110 may have either a free configuration or a fixed configuration. In the free configuration, any types of containers 325 (with fluorescence agent of any nature and concentration) may be arranged in the seats 320. In a fixed configuration, instead, pre-defined types of containers 325 (with fluorescence agent of specific nature and concentration) are to be arranged in the seats 320. In the latter case, one or more of the markers 340,345 (either individually or in combination) encode (unique) container identifiers of the types of containers 325 to be accommodated in the seats 320 (for example, with each container identifier encoded in a corresponding marker 345 close to its seat 320). The container identifiers allow verifying the correct configuration of the testing device 110.

The markers 340,345 are arranged at corresponding bottom surfaces of recesses (denoted with the same references), which extend from the imaging surface 315 inwards the holder 305 (downwards). The bottom surfaces of the recesses 340,345 are parallel to the resting surface 310. Therefore, when the testing device 110 rests on the supporting surface 175 (substantially horizontally), the bottom surfaces of the recesses 340,345 are horizontal as well. This increases a visibility of the markers 340,345 (when observed from above). Moreover, the recesses 340,345 have corresponding edges at the imaging surface 315 which are chamfered. For example, the edges are chamfered to form an angle of 40-50° (such as of 45°) with the imaging surface 315. This reduces any shadowing of the markers 340,345 when the testing device 110 is illuminated from above.

The testing device 110 comprises a testing light source 350 at the imaging surface 315, which testing light source 350 generates a testing light of the same type as the fluorescence light emitted by one or more fluorescence agents when illuminated by the excitation light (i.e., of NIR type). For example, the testing light source 350 is based on a frame of LEDs running around the marker 340; the testing light source 350 is supplied by a replaceable/non-replaceable battery enclosed in the holder 305 and is turned on/off by acting on a switch (not visible in the figure). The testing light source 350 may be used to test the acquisition unit of the imaging apparatus alone (with its illumination unit turned off).

In the fixed configuration of the testing device 110, the holder 305 has corresponding seat indicators 355 on the imaging surface 315 (for example, formed by corresponding labels stitched thereon), which are human-readable (for example, in text form). The seat indicators 355 are arranged in correspondence to the seats 320 and provide a specification of the types of containers 325 to be accommodated therein. Particularly, the seat indicators 355 are color-coded; for example, the seat indicators 355 contain color names corresponding to the types of containers 325 (such as white, yellow, blue and green for increasing concentrations of a same fluorescence agent). The seat indicators 355 facilitate the insertion of the correct types of containers 325 into the seats 320 (especially when the testing device 110 is assembled on the field).

In any (free/fixed) configuration of the testing device 110, the containers 325 have corresponding container indicators, which are human-readable (for example, colors). The container indicators are arranged on parts of the containers 325 projecting from the seats 320 when the containers 325 are inserted therein (so as to remain visible) and provide a specification of their types. Particularly, the container indicators are again color-coded. For example, the caps 430 are colored according to the types of containers 320 as above, i.e., white, yellow, blue and green for increasing concentrations of the fluorescence agent (in this case, discernible by people affected by protanopia as well). The container indicators further facilitate the insertion of the correct types of containers 325 in the corresponding seats 320; moreover, they also allow verifying that the testing device 110 has been assembled correctly at any time.

Figure 5:
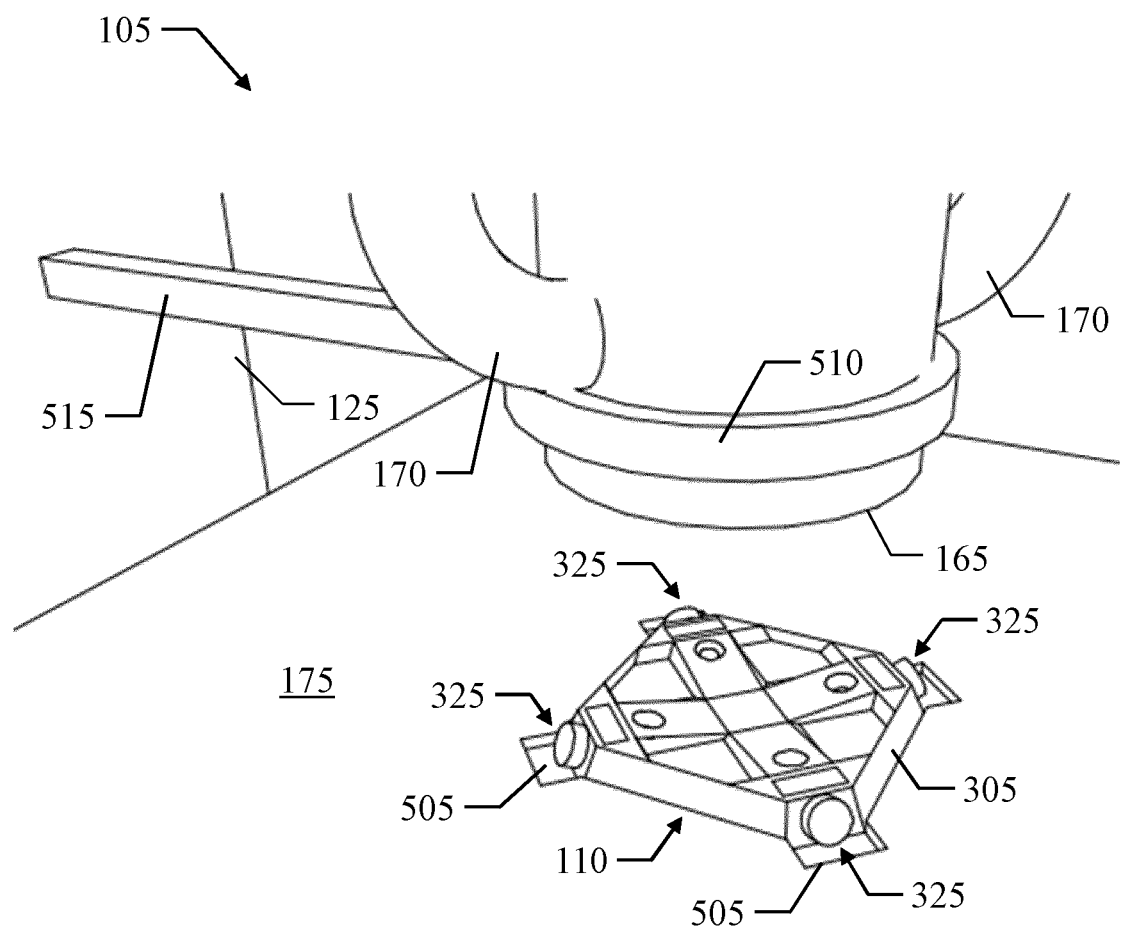
FIG. 5 shows a detail of the fluorescence imaging apparatus according to an embodiment of the present disclosure.

With reference now to FIG. 5, a detail is shown of the imaging apparatus 105 according to an embodiment of the present disclosure.

The imaging apparatus 105 has a holding station 505, which is used to hold the testing device 110 in a fixed (imaging) position on the supporting surface 175; the testing device 110 is held in the imaging position in a removable way. For example, the holding station 505 is formed by a recess matching a footprint of the testing device 110 (defined by its resting surface, not visible in the figure), possibly with the addition of four lateral hollows for avoiding any interference of the parts of the containers 325 projecting from the holder 305; in this way, the testing device 110 may be inserted into the holding station 505 by dropping it into the recess. The recess has a depth lower than a height of the holder 305; in this way, the testing device 110 may be removed from the holding station 505 by grasping and lifting it from the recess.

Moreover, the imaging apparatus 105 has a (further) holding station 510, which is used to hold the imaging head 165 in an (acquisition) position; the imaging head 165 as well is held in the acquisition position in a removable way. For example, the holding station 510 is formed by a ring matching a main body of the imaging head 165 (excluding its handlebars 170); the ring is integral with a cantilever 515 fixed to the pillar 125 of the testing device 110. In this way, the imaging head 165 may be inserted into the holding station 510 by sliding it into the ring from above, until the handlebars 170 abut against it; moreover, the imaging head 165 may be removed from the holding station 510 by lifting it until leaving the ring.

Alternatively (not shown in the figure), the holding station 505 and the holding station 510 may be combined into a single structure for holding both the testing device 110 in the imaging position and the imaging head 165 in the acquisition position. For example, this result may be achieved by a cylinder which is closed at the bottom by a base having a recess for inserting the testing device 110 and it is open at the top for sliding the imaging head 165 as above.

When the testing device 110 is in the imaging position (defined by the holding station 505) and the imaging head 165 is in the acquisition position (defined by the holding station 510), the testing device 110 falls within the field of view of the imaging head 165. Particularly, the central point of the holder 305 is on the optical axis of the imaging head 165. This provides a controlled and repeatable illumination of the testing device 110.

Figure 6:
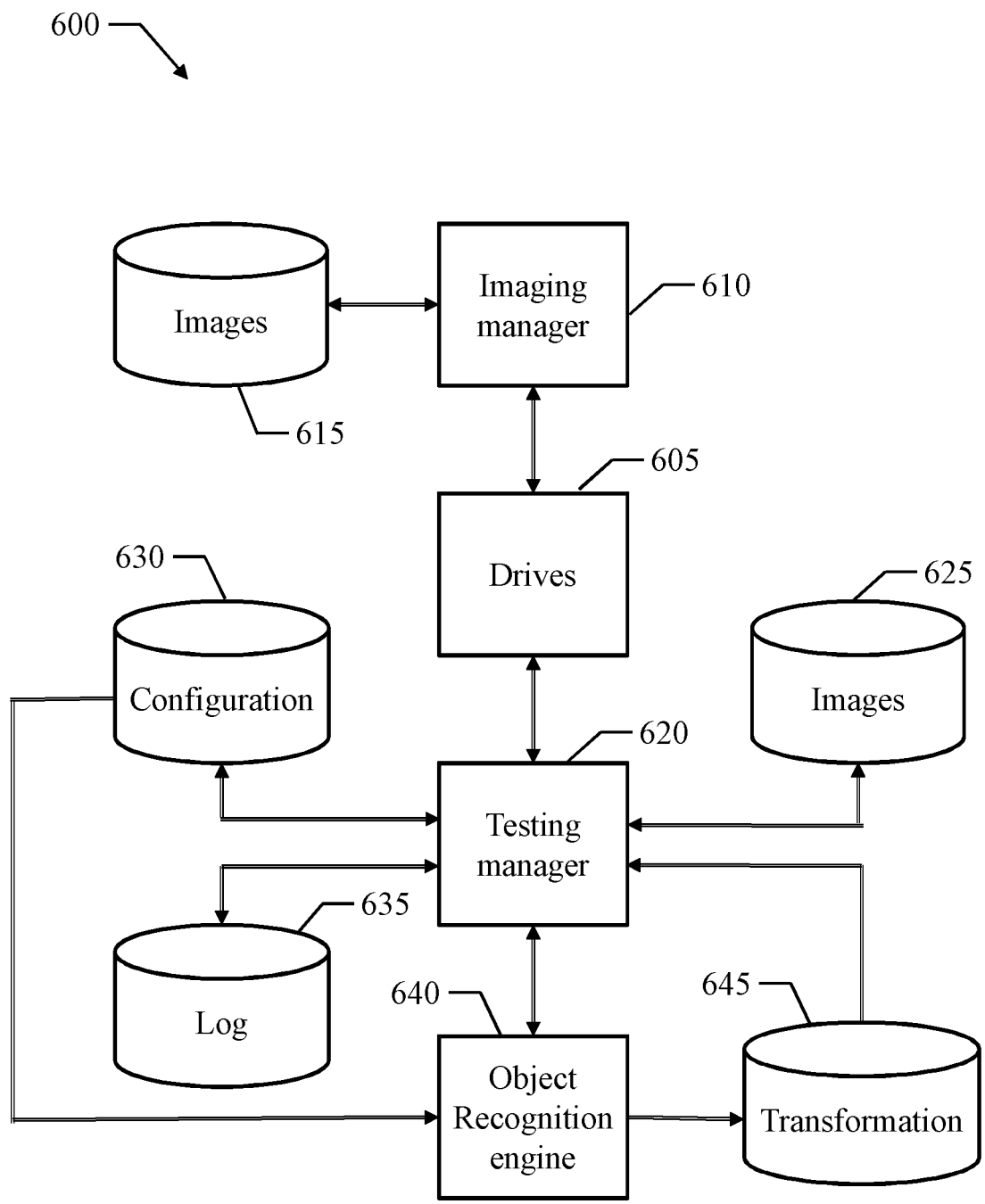
FIG. 6 shows the main software components that may be used to implement the solution according to an embodiment of the present disclosure.

With reference now to FIG. 6, the main software components are shown that may be used to implement the solution according to an embodiment of the present disclosure.

All the software components (programs and data) are denoted as a whole with the reference 600. The software components 600 are typically stored in the mass memory and loaded (at least in part) into the working memory of the control unit of the imaging apparatus when the programs are running, together with other software components not directly relevant to the solution according to the present disclosure (such as an operating system, medical applications and so on), which other software components are omitted for the sake of simplicity. The programs are initially installed into the mass memory, for example, from removable storage units or from the communication network (not shown in the figure). In this respect, each program may be a module, segment or portion of code, which comprises one or more executable instructions for implementing the specified logical function.

Particularly, corresponding drives, denoted as whole with the reference 605, are used to drive the peripherals of the imaging apparatus, comprising its excitation light source, white light source, fluorescence camera, photograph camera, keyboard, pointing device, primary/secondary monitors and network interface card. An imaging manager 610 manages imaging processes of any body-parts. The imaging manager 610 interfaces with the drives 605. The imaging manager 610 accesses (in read/write mode) an imaging repository 615, which stores a sequence of fluorescence images and photograph images being acquired during an imaging process that is in progress.

In the solution according to an embodiment of the present disclosure, a testing manager 620 manages any tests of the imaging apparatus. The testing manager 620 as well interfaces with the drives 605. The testing manager 620 accesses (in read/write mode) an image repository 625, a configuration repository 630 and a log repository 635. The image repository 625 stores one or more fluorescence images and photograph images that are acquired during a test of the imaging apparatus that is in progress. The configuration repository 630 stores configuration information for the tests of the imagining apparatus. For example, the configuration information comprises a network address (such as a domain name) of a remote service provider (for example, a server of a manufacturer of the imaging apparatus), a descriptor of the testing device and a descriptor of the containers. The descriptor of the testing device indicates it by the corresponding device identifier. The descriptor of the testing device defines its configuration, i.e., free or fixed. The descriptor of the testing device defines its geometry; for example, the geometry of the testing device is defined in terms of shape of its holder and in terms of position of the windows, the markers, the seat indicators and the caps with respect to the holder (i.e., their real-word coordinates in a reference system integral therewith). The descriptor of the testing device defines a specification of the containers for the markers, the seat indicators and the container indicators; for example, for each possible type of container there are provided its container identifier for the markers, its color name for the corresponding seat indicator and its color definition for the corresponding container indicator (the latter in terms of nominal values of one or more statistical parameters relating thereto, such mean value of color components, like RGB components). The descriptor of the testing device defines one or more usage rules thereof (for example, maximum usage in terms of length of the tests, maximum elapsed time from a production date and so on). The descriptor of the testing device defines one or more characteristics of each testing light generated by its testing light source (for example, wavelength and nominal values of one or more statistical parameters relating thereto, such as mean fluorescence intensity, or MFI). The descriptor of the containers defines each possible type of them; for example, each type of container (identified by its container identifier) is defined by nature and/or concentration of the corresponding fluorescence agent and by a fluorescence specification of the fluorescence light emitted by it (wavelength and nominal values of one or more statistical parameters relating thereto, such as mean fluorescence intensity). The log repository 635 stores information about the tests that have been performed by the imaging apparatus 105. For example, the log repository 635 has a record for each test (for example, identified by its timestamp); the record comprises a length of the test, an indication of a result of the test and a change flag (which is asserted when the test has been performed with a new testing device and/or with new containers). The testing manager 620 exploits an object recognition engine 640, which is used to find the position of the testing device in photograph/fluorescence images thereof. The object recognition engine 640 accesses (in read mode) the configuration repository 630 and it accesses (in write mode) a transformation repository 645, which is also accessed (in read mode) by the testing manager 620. The transformation repository 645 stores a definition of a transformation between the real-word coordinates of the testing device and corresponding image coordinates in the fluorescence/photograph images (for example, in the form of a transformation matrix).

Figure 7A:
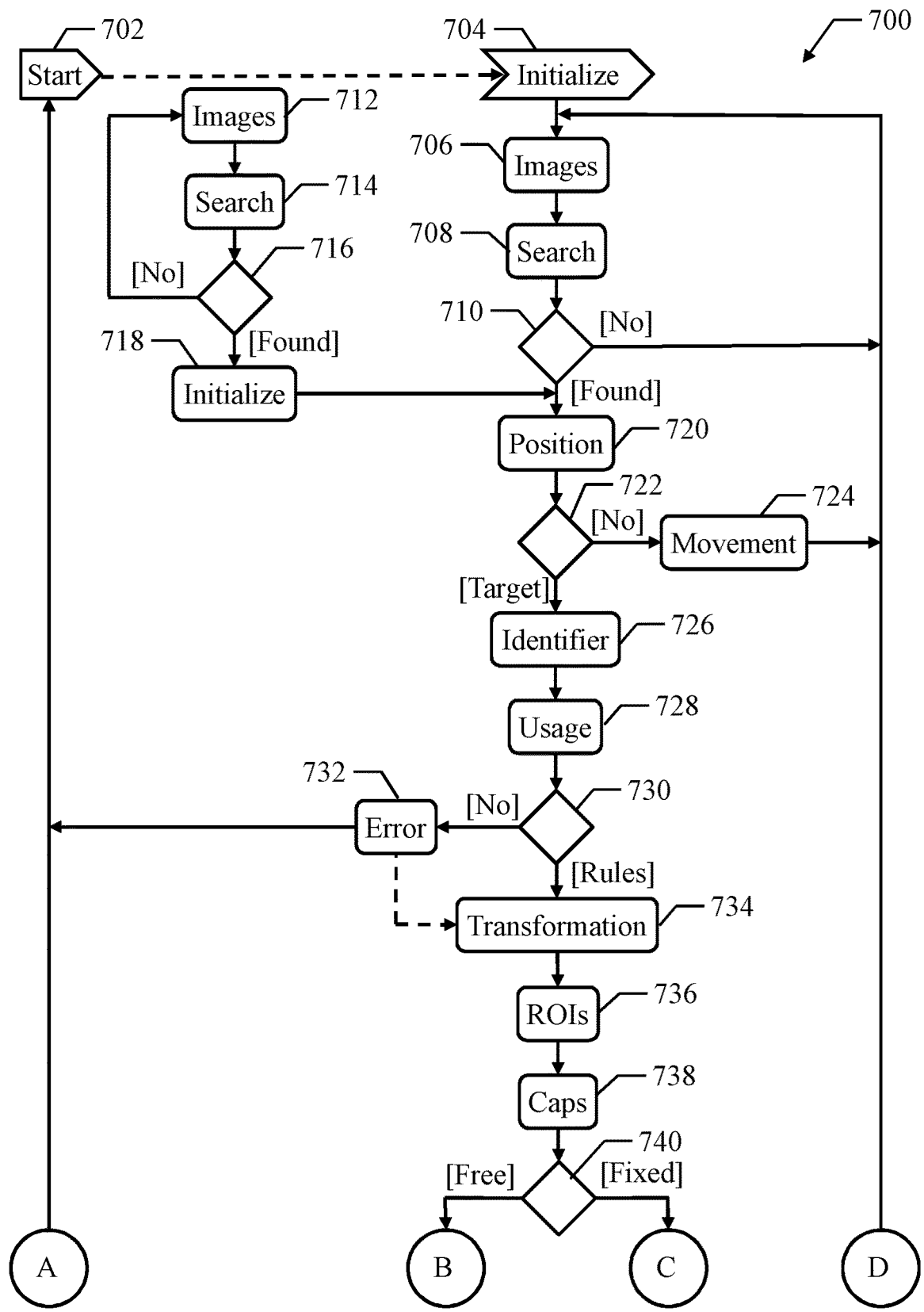
FIG. 7A-FIG. 7C show an activity diagram describing the flow of activities relating to an implementation of the solution according to an embodiment of the present disclosure.
Figure 7B:
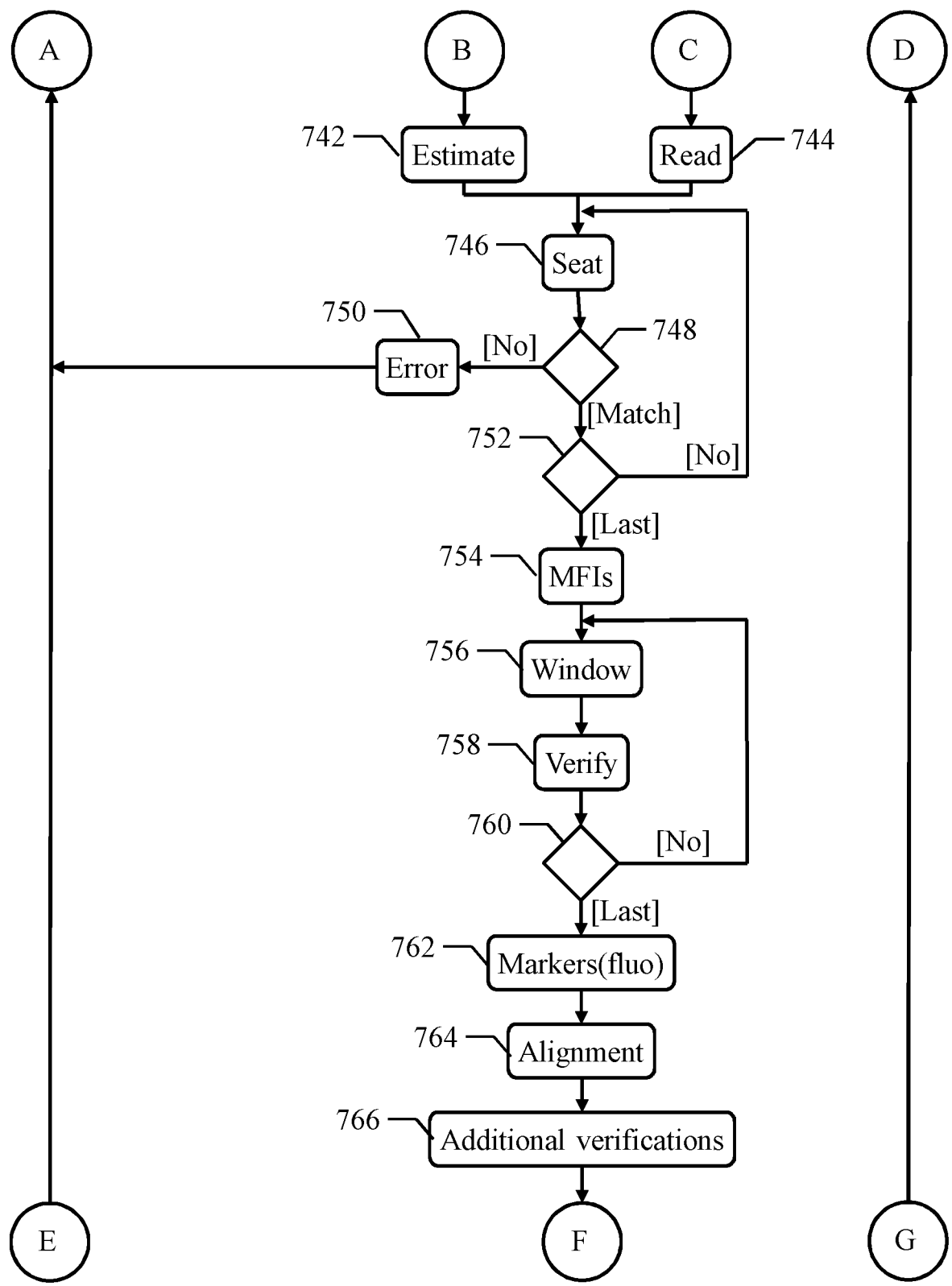
Figure 7C:
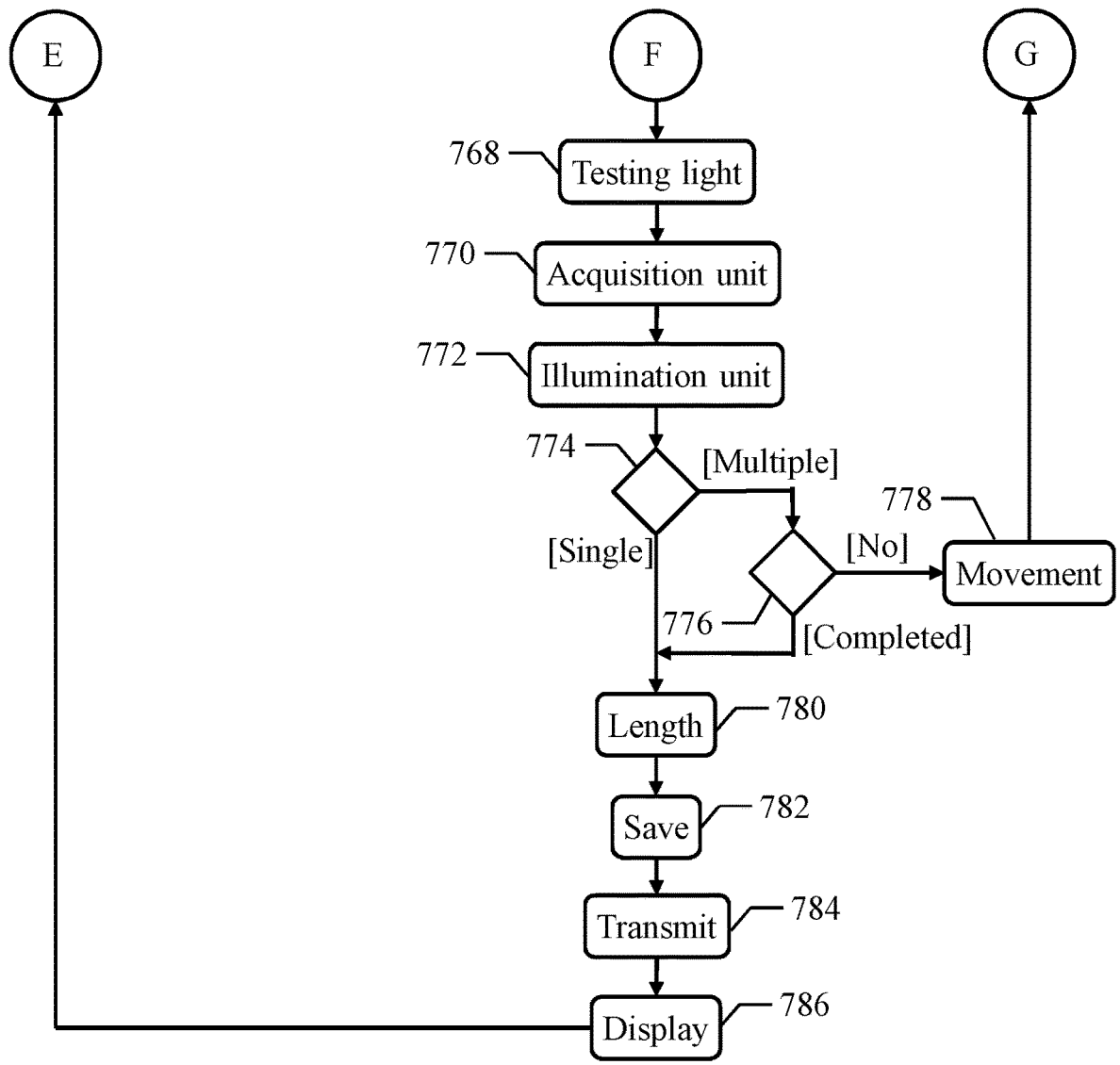

With reference now to FIG. 7A-FIG. 7C, an activity diagram is shown describing the flow of activities relating to an implementation of the solution according to an embodiment of the present disclosure.

Particularly, the activity diagram represents an exemplary process that may be used to test the imaging apparatus with a method 700. In this respect, each block may correspond to one or more executable instructions for implementing the specified logical function on the control unit of the imaging apparatus.

The process is executed whenever the imaging apparatus has to be tested. For example, this may happen before any imaging process, after an installation or any maintenance of the imaging apparatus, upon request, periodically and so on, either in response to a corresponding request or automatically (as described in the following).

In this event, the operator places the testing device onto the supporting surface and the imaging head above it (for example, by inserting the testing device and the imaging head into the corresponding holding stations if available). The operator then enters a test command with the keyboard or the pointing device; the test command may also specify a type of the test, selected between a test in a single position or a test throughout the field of view of the imaging head (for example, the first one by default). At the same time, the operator may also select a corresponding command when the containers or the whole testing device have been changed, in the latter case together with its device identifier. In any case, the test command is received at block 702 by the testing manager via the corresponding drive.

In response thereto, the process passes to block 704 wherein the testing manager initializes a temporary record for the test, with its time-stamp (set to a current time from an internal clock), start time (set to the same current time) and change flag (asserted if the containers or the testing device have been changed or deasserted otherwise); moreover, if the testing device has been changed, the testing manager downloads an indication of the (free/fixed) configuration of the testing device from the service provider (from its network address retrieved from the configuration repository) according to the device identifier, and then updates the descriptor of the testing device in the configuration repository accordingly. The testing manager at block 706 turns on the white light source and the excitation light source, and it commands the photograph camera and the fluorescence camera to acquire a photograph image and a fluorescence image, respectively, of their same field of view (via the corresponding drives), after that the testing manager turns off the white light source and the excitation light source. The photograph image is defined by a bitmap comprising a matrix of cells (for example, with 512 rows and 512 columns) each storing a value of a pixel, i.e., a basic picture element corresponding to a location of the field of view, which pixel value represents the visible light reflected by the location (such as its RGB components). The fluorescence image is defined by a bitmap comprising a matrix of cells (with either the same or different size with respect to the photograph image) each storing a pixel value representing the fluorescence light emitted by the corresponding location of the field of view (such as its intensity). The object recognition engine at block 708 searches for the testing device in the photograph image, i.e., its representation in a corresponding Region Of Interest (ROI), by exploiting image processing techniques known per se based on the known geometry of the testing device (as defined by its descriptor in the configuration repository). The testing manager at block 710 verifies whether the testing device has been found. Particularly, the image recognition engine may simply search for the holder of the testing device (according to its shape). In addition or in alternative, the image recognition engine searches for the markers (according to their specification) and verifies whether they are correct (i.e., in the right number and with the right format). The markers make the detection of the testing device more accurate (with respect to the use of the holder), especially when they are multiple (like the five markers in the example at issue). If the testing device has not been found (i.e., no holder and/or no correct markers), the process returns to the block 706 to repeat the same operations continually, up to a pre-defined time-out, after that the process returns to the block 702 (not shown in the figure) with the testing manager that displays an error message on the primary monitor (via the corresponding drive).

The same operations may also be performed to start the test automatically in response to an appearance of the testing device within the field of view of the imaging head. For this purpose, in a non-operative condition of the imaging apparatus (i.e., when no imaging process is in progress), the testing manager monitors the field of view by continually performing a corresponding loop. The loop begins at block 712, wherein the testing manager turns on the white light source and the excitation light source, and it commands the photograph camera and the fluorescence camera to acquire a photograph image and a fluorescence image, respectively, of their same field of view (via the corresponding drives), after that the testing manager turns off the white light source and the excitation light source. The object recognition engine at block 714 searches for the testing device in the photograph image as above. The testing manager at block 716 verifies whether the testing device has been found. If the testing device has not been found, the process returns to the block 712 to repeat the same operations periodically (for example, every 5-10 s). Conversely, as soon as the testing device has been found, the process descends into block 718. At this point, the testing manager initializes the temporary record with its time-stamp and start time as above, and with the type of test set to the single position and the change flag deasserted. This allows starting the test by simply presenting the testing device into the field of view of the imaging head, without the need of any additional intervention by the operator.

In any case, the process continues to block 720 from the block 710 (as soon the testing device has been found) or from the block 718. At this point, the testing manager determines a current position of the testing device with respect to the imaging head according to its representation in the photograph image (with image-processing techniques known per se); for example, the current position is defined by a location of the central point of the testing device in an imaging plane perpendicular to the optical axis of the imaging head, a distance of the testing device from the imaging head and a rotation angle of the testing device with respect to the imaging plane. This operation is completely automatic, and then fast and accurate. The testing manager at block 722 verifies whether the current position matches a target position (such as defined by the central point of the testing device on the optical axis of the imaging head, the testing device at a certain distance from the imaging head and parallel to its imaging plane). For example, the testing manager calculates a corresponding displacement between the current position and the target position as defined by translation and rotation components, and compares them with corresponding pre-defined thresholds (such as 0.1-1 cm and 1-5°). If one or more translation/rotation components exceed the corresponding thresholds (meaning that the current position does not match the target position), the testing manager at block 724 displays a corresponding message on the primary monitor (via the corresponding drive). The message indicates a movement of the testing device and/or of the imaging head (given by the displacement), which is required for reaching the target position; for example, when the central point of the testing device is not on the optical axis of the imaging head, the operator is required to translate it, whereas when the testing device is not at the correct distance/angle with respect to the imaging head, the operator is required to translate/rotate the latter. The process then returns to the block 706 to repeat the same operations. In this way, the operator is provided with a very useful feedback, which allows placing the testing device and/or the imaging head in a correct reciprocal position even when no holding stations are available.

Referring back to the block 722, if all the translation/rotation components do not exceed the corresponding thresholds (meaning that the current position matches the target position), the process descends into block 726; particularly, this is always true when the testing device and the imaging head are inserted into the corresponding holding stations. At this point, the testing manager extracts the device identifier from the markers in the photograph image. The testing manager at block 728 retrieves usage information of the testing device from the log repository (for example, length of the tests that have been performed since a last change of the testing device or of its containers). In addition or in alternative, the testing manager downloads (further) usage information of the testing device from the service provider (from its network address retrieved from the configuration repository) according to its device identifier (assuming that it matches the one stored in the configuration repository); for example, this usage information may comprise an authenticity indicator of the testing device and its production date. The testing manager at block 730 verifies the usage information (retrieved and/or downloaded) against the usage rules (retrieved from the configuration repository); for example, the testing manager compares the length of the tests (since the last change of the testing device or of its containers) and/or a time elapsed from the production date with the corresponding maximum allowable values. The testing monitor then enables the test according to a result of this verification. If any usage rule is not satisfied (always true when the device identifier does not match the one stored in the configuration repository), the testing manager at block 732 aborts the test and displays a corresponding error message on the primary monitor (via the corresponding drive); the process then returns to the block 702 waiting for a next test command. Alternatively, as shown in dashed line in the figure, the testing manager simply displays a corresponding warning message on the primary monitor (via the corresponding drive), but the test is still allowed by continuing to block 734. The same point is also reached directly from the block 730 if all the usage rules are satisfied.

At this point, the testing manager generates the transformation matrix (between the real-word coordinates of the testing device and the image coordinates in its fluorescence/photograph images); for example, the transformation matrix is calculated by minimizing a mapping error between the real-word coordinates of the markers in the testing device (retrieved from the configuration repository) and the image coordinates of the markers in the photograph image (such as the mean square value of their differences). This operation may be based on a single marker with asymmetric readout (providing location and orientation of the testing device according to its specification); however, the use of multiple markers (like the five markers in the example at issue) adds further accuracy. The testing manager at block 736 further determines the seat indicators and the caps in the photograph image and the windows in the fluorescence image (i.e., their representations in corresponding ROIs) according to their image coordinates therein calculated by applying the transformation matrix to the corresponding real-word coordinates (retrieved from the configuration repository). This operation is completely automatic, and then fast and accurate.

The testing manager now verifies the containers arranged in the seats. For this purpose, the testing manager at block 738 calculates the same statistical parameters, of the color definitions for the container indicators in the configuration repository, for the pixel values representing each cap in the photograph image, i.e., mean values of their RGB components in the example at issue. The flow of activity branches at block 740 according to the configuration of the testing device (retrieved from the configuration repository). If the testing device has the free configuration, the testing manager at block 742 estimates the types of containers arranged in the seats. For example, the testing manager calculates a distance between the colors of the caps in the photograph image and the color definitions of every permutation of four types of containers among all the possible ones defined in the configuration repository (such as equal to the mean square value of the differences between the mean values of the RGB components of each cap and the corresponding nominal values of the color definition of the corresponding type of container); the testing manager selects the permutation that provides the lowest distance. Referring back to the block 740, if the testing device has the fixed configuration, the testing manager at block 744 extracts the container identifiers from the markers in the photograph image (indicating the types of containers that should be arranged in the seats). In this phase, the testing manager may also read the color names from the seat indicators in the photograph image (indicating the same expected types of containers that should be arranged in the seats). The testing manager verifies whether each pair of corresponding color name and container identifier refers to the same type of container (as indicated in the configuration repository). If not, the process returns to the block 702 (not shown in the figure) with the testing manager that displays an error message on the primary monitor (via the corresponding drive). In this way, it is possible to ensure that the testing device (in the fixed configuration) has been assembled correctly. The flow of activity then merges at block 746 from either the block 742 or the block 744; at this point, a loop is entered with the testing manager that takes a (current) seat into account (starting from a first one in any arbitrary order). The testing manager at block 748 verifies whether the container arranged in the seat is of the expected type (i.e., the estimated one in the free configuration or the read one in the fixed configuration). For this purpose, the testing manager verifies whether the color of the cap matches the color definition of the expected type of container (retrieved from the configuration repository); for example, the testing manager calculates a difference between the mean value of each RGB component of the cap and the corresponding nominal value of the color definition, and compares them with a pre-defined threshold (such as 1-5% with respect to the color definition). If one or more differences exceed the threshold (meaning that the container is not of the expected type), the testing manager at block 750 aborts the test and displays a corresponding error message on the primary monitor (via the corresponding drive); the process then returns to the block 702 waiting for a next test command. Conversely, if no difference exceeds the threshold (meaning that the container is of the expected type), the testing manager at block 752 verifies whether a last seat has been processed. If not, the process returns to the block 746 to repeat the same operations for a next seat. Conversely, once all the seats have been processed (determining that all the containers of the expected types are arranged therein), the loop is exit by descending into block 754.

At this point, the testing manager verifies the windows in the fluorescence image. For this purpose, the testing manager calculates the same statistical parameters, of the fluorescence specification for the corresponding type of container in the configuration repository, for the pixel values representing each window in the fluorescence image, i.e., mean fluorescence intensity in the example at issue; moreover, the testing manager calculates the same statistical parameters (i.e., mean fluorescence intensity) for the pixel values representing a background area different from the windows in the photograph image (for example, coincident with the central marker). A loop is then entered at block 756 with the testing manager that takes a (current) window into account (starting from a first one in any arbitrary order). The testing manager at block 758 verifies whether the window matches the fluorescence specification of the type of container arranged in the seat (retrieved from the configuration repository); for example, the testing manager calculates a difference between the mean fluorescence intensity of the window and the corresponding nominal value of the type of container, and compares it with a pre-defined threshold (such as 1-5% with respect to the fluorescence specification). In addition or in alternative, the testing manager calculates the ratios between the mean fluorescence intensity of the (current) window and the mean fluorescence intensity of each other window and of the background area; the testing manager further calculates the ratios between the corresponding nominal values (retrieved from the configuration repository for the types of containers of the other windows and set to almost zero for the background area). The testing manager then calculates a difference between each pair of ratios, and compares it with a pre-defined threshold (such as 1-5% with respect to the ratio of the nominal values). In any case, the testing manager adds a result of these verifications to the temporary record for the test. The testing manager at block 760 verifies whether a last window has been processed. If not, the process returns to the block 756 to repeat the same operations for a next window. Conversely, once all the windows have been processed, the loop is exit by descending into block 762.

At this point, the testing manager verifies an alignment between the photograph image and the fluorescence image. For this purpose, the object recognition engine searches for the markers (i.e., their representations in corresponding ROIs) in the fluorescence image (as above). The testing manager at block 764 verifies whether the markers in the photograph image match the corresponding markers in the fluorescence image; for example, the testing manager calculates a distance between each marker in the photograph image and in the fluorescence image as defined by a mean value of corresponding translation components, and compares it with a pre-defined threshold (such as 1-5% of a maximum extent of the marker in the photograph image). The testing manager adds a result of this verification to the temporary record of the test.

The testing manager at block 766 may perform additional verifications of the imaging apparatus (according to the photograph image). For example, the testing manager determines a contrast of the acquisition unit according to a difference between the brightest pixel values and the least bright pixel values of the marks in the photograph image. In case the marks are tilted with respect to the row/columns of the photograph image (by an angle known from the geometry of the testing device retrieved from the configuration repository), the testing device determines the depth of field of the acquisition unit by applying the slanted edge method. The testing device may have a spatial resolution target on its imaging surface (for example, the 1951 USAF, IEEE or ISO one), which is further specified in the configuration repository; in this case, the object recognition engine searches for the spatial resolution target (i.e., its representation in a corresponding ROI) in the photograph image, and the testing manager then determines the spatial resolution of the acquisition unit according thereto. The testing device may have a color test target on its imaging surface (either distinct or combined with the spatial resolution target), which is further specified in the configuration repository; in this case, the object recognition engine searches for the color test target (i.e., its representation in a corresponding ROI) in the photograph image, and the testing manager then determines the color resolution of the acquisition unit according thereto. The testing device may have a reflectance standard on its imaging surface (either distinct or combined with the spatial resolution target and/or the color target), which is further specified in the configuration repository. In this case, the object recognition engine searches for the reflectance standard (i.e., its representation in a corresponding ROI) in the photograph image. The testing manager determines an ambient light as a difference between the white light generated by the white light source (as further defined in the configuration repository in terms of one or more statistical parameters relating thereto, such as its mean intensity) and a corresponding reflected light received from the reflectance standard (as defined by the same statistical parameters for the pixel values representing it in the photograph image, i.e., mean intensity in the example at issue). The testing manager then compares the ambient light (defined by the values of the statistical parameters for the reflected light minus the values of the corresponding statistical parameters for the white light) with a pre-defined threshold (such as 1-5% of the values of the statistical parameters for the white light). In addition or in alternative, the same operation may also be performed by determining the ambient light as a difference between the excitation light generated by the excitation light source (as further defined in the configuration repository in terms of one or more statistical parameters relating thereto, such as its mean intensity) and a corresponding (further) reflected light received from the reflectance standard (as defined by the same statistical parameters for the pixel values representing it in the fluorescence image, i.e., mean intensity in the example at issue). This allows verifying that the ambient conditions are suitable for correct operation of the imaging apparatus. In any case, the testing manager adds a result of these verifications to the temporary record of the test.

The testing manager at block 768 displays a message on the primary monitor (via the corresponding drive), requiring the operator to turn on the testing light source (via the corresponding switch of the testing device). As soon as the testing light source has been turned on, the process continues to block 770. For example, this may happen in response to a corresponding command entered by the operator with the keyboard or the pointing device (received by the testing manager via the corresponding drive). Alternatively, this may happen automatically by monitoring the field of view with a corresponding loop which is performed continually (for example, every 1-2 s). Particularly, for this purpose the testing manager commands the fluorescence camera to acquire a fluorescence image of its field of view with the excitation light source turned off (via the corresponding drives) and then calculates the mean intensity of the fluorescence image; these operations are repeated until the mean intensity exceeds a threshold, such as 2-3 times the one corresponding to typical ambient fluorescence. In both cases, the testing manager now commands the fluorescence camera to acquire a (further) fluorescence image of its field of view (via the corresponding drives), while the white light source and the excitation light source are turned off. The testing manager verifies the acquisition unit alone of the imaging apparatus according to this luminescence image and the characteristics of the testing light (retrieved from the configuration repository); for example, the testing manager calculates a difference between the mean fluorescence intensity of the fluorescence image and its nominal value, and then compares this difference with a pre-determined threshold (such as 5-10% with respect to the nominal value). The testing manager adds a result of this verification to the temporary record of the test. The testing manager at block 772 verifies the illumination unit alone of the imaging apparatus according to the above-mentioned verifications of the imaging apparatus (as a whole) and of its acquisition unit (alone). For example, the testing manager conditions the statistical parameters (mean fluorescence intensity) calculated above for the pixel values representing each window in the previous fluorescence image (step 754) according to the difference between the same mean fluorescence intensity of the (current) fluorescence image and its nominal value (so as to remove the effect of any mismatch of the acquisition unit); the testing manager then verifies again whether each window matches the fluorescence light emitted by the container arranged in the corresponding seat as above (steps 756-760). The testing manager adds a result of this verification to the temporary record of the test.

The flow of activity branches at block 774 according to the type of test (as indicated in the temporary record). If the test has to be performed throughout the field of view of the imaging head, the testing manager at block 776 verifies whether it has been completed (i.e., the imaging apparatus has already been tested in all a set of predefined positions throughout the field of view, such as in a matrix with a pitch of 1-5 cm along every direction). If not, the testing manager at block 778 determines a movement of the testing device (according to the pitch) for reaching a further (new) position throughout the field of view; the testing manager then displays a corresponding message on the primary monitor (via the corresponding drive). As soon as the testing device has been moved to the new position, the process returns to the block 706 to repeat the same test of the imaging apparatus in its new position. For example, this may happen in response to a corresponding command entered by the operator with the keyboard or the pointing device (received by the testing manager via the corresponding drive). Alternatively, this may happen automatically by monitoring the field of view with a corresponding loop which is performed continually (for example, every 1-2 s). Particularly, for this purpose the testing manager turns on the white light, commands the photograph camera to acquire a photograph image of its field of view and then turns off the white light source (via the corresponding drives), the object recognition engine searches for the testing device in the photograph image, the testing manager verifies whether the testing device has been found and if so whether the current position of the testing device matches the new position (as above); these operations are repeated until the testing device has been found in the new position. The process instead descends into block 780 from the block 776 once the test has been completed (in all the positions throughout the field of view) or directly from the block 774 if the test has to be performed in a single position. In any case, the testing manager now determines a length of the test, from its start time (from the temporary record) to the current time (from the internal clock); the testing manager adds the length of the test to the temporary record.

The testing manager at block 782 saves the result of the test defined in the temporary record by adding it to the log repository. The testing manager at block 784 transmits the result of the test to the service provider (to its network address retrieved from the configuration repository). This allows implementing telemetric applications for tracking operation of the imaging apparatus remotely. The testing manager at block 786 displays the result of the test on the primary monitor (via the corresponding drive). The operator may then react accordingly. For example, if the result of the test indicates that the performance of the imaging apparatus is good, the corresponding imaging process may be performed (with a high degree of confidence on the information provided by the imaging apparatus). Conversely, the imaging process is aborted (since the information provided by the imaging apparatus might be misleading) and the operator may request an intervention to a support center of the manufacturer of the imaging apparatus. The process then returns to the block 702 waiting for a next test command.

All of the above allows verifying the performance of the imaging apparatus with a high accuracy and in a reproducible manner. In this way, it is possible to detect any degradation of the performance of the imaging apparatus (for example, caused by corrupted light sources, dirty delivery/collection optics, mechanical wearing, parasitic light and so on), even when the degradation is not noticeable by the operator.

MODIFICATIONS

Naturally, in order to satisfy local and specific requirements, a person skilled in the art may apply many logical and/or physical modifications and alterations to the present disclosure. More specifically, although this disclosure has been described with a certain degree of particularity with reference to one or more embodiments thereof, it should be understood that various omissions, substitutions and changes in the form and details as well as other embodiments are possible. Particularly, different embodiments of the present disclosure may even be practiced without the specific details (such as the numerical values) set forth in the preceding description to provide a more thorough understanding thereof, conversely, well-known features may have been omitted or simplified in order not to obscure the description with unnecessary particulars. Moreover, it is expressly intended that specific elements and/or method steps described in connection with any embodiment of the present disclosure may be incorporated in any other embodiment as a matter of general design choice. Moreover, items presented in a same group and different embodiments, examples or alternatives are not to be construed as de facto equivalent to each other (but they are separate and autonomous entities). In any case, each numerical value should be read as modified according to applicable tolerances; particularly, unless otherwise indicated, the terms "substantially", "about", "approximately" and the like should be understood as within 5-10%. Moreover, each range of numerical values should be intended as expressly specifying any possible number along the continuum within the range (comprising its end points). Ordinal or other qualifiers are merely used as labels to distinguish elements with the same name but do not by themselves connote any priority, precedence or order.

The terms include, comprise, have, contain, involve and the like should be intended with an open, non-exhaustive meaning (i.e., not limited to the recited items), the terms based on, dependent on, according to, function of and the like should be intended as a non-exclusive relationship (i.e., with possible further variables involved), the term a/an should be intended as one or more items (unless expressly indicated otherwise), and the term means for (or any means-plus-function formulation) should be intended as any structure adapted or configured for carrying out the relevant function.

For example, an embodiment provides a testing device for testing a luminescence imaging apparatus. However, the testing device may be of any shape (for example, with point symmetry or not), size and material (for example, plastic, resin, metal and so on); moreover, the testing device may be used to test any luminescence imaging apparatus for any purpose (see below).

In an embodiment, the testing device comprises a resting surface for resting the testing device on a supporting surface. However, the resting surface may be of any type (for example, continuous or discontinuous, flat, defined by projecting support elements, such as feet, balls and the like, with recesses, and so on) and it may be used to rest the testing device in any way (for example, freely, in a holding station, locked thereto, and so on) on any supporting surface (either part of the luminescence imaging apparatus or separate therefrom, such as a table, a shelf and so on).

In an embodiment, the testing device comprises one or more seats. However, the seats may be in any number, of any shape (for example, with any section, such as circular, squared and so on, being constant, varying or both of them), of any size and at any position (for example, open laterally, on the bottom, arranged regularly or not, and so on)

In an embodiment, the testing device comprises one or more containers each filled with a liquid comprising at least one luminescence substance. However, the containers may be of any shape/size (either the same as or simply compatible with the ones of the seats), of any material (for example, of plastic, glass and so on) and of any type (for example, vials, tubes, bottles and so on); moreover, the containers may be filled at any level with any liquid containing any number and type of luminescence substances (for example, based on any luminescence phenomenon, such as fluorescence, phosphorescence, chemiluminescence, bio-luminescence, induced Raman-radiation, with the containers filled with the same luminescence substances in different concentrations and/or with different luminescence substances, and so on).

In an embodiment, each of the containers is accommodated in a corresponding one of the seats. However, the containers may be in any number (either the same or lower than the number of the seats) and they may be accommodated in the seats in any way (for example, in a removable way, non-removable way, a combination thereof, and so on).

In an embodiment, the testing device comprises one or more windows corresponding to the seats. However, the windows may be of any type (for example, with or without chamfered edges), size and shape (for example, circular, squared and so on).

In an embodiment, the windows are opened in an imaging surface of the testing device opposite the resting surface. However, the imaging surface may be of any type (for example, continuous or discontinuous, flat or non-flat, parallel or inclined with respect to the resting surface, and so on).

In an embodiment, each of the windows exposes a part of the corresponding seat for imaging the luminescence substance of a corresponding part of the container accommodated therein being transparent to an excitation light of the luminescence substance and to a luminescence light emitted by the luminescence substance when illuminated by the excitation light. However, the exposed part of each seat may have any extent (up to the whole seat excluded at the distal end thereof). The containers may be transparent (at any extent) in any part thereof comprising the one to be imaged through the windows (up to completely), to any wavelengths comprising the ones of the excitation/luminescence light (for example, to the visible light as well).

In an embodiment, the seats extend along corresponding longitudinal axes from corresponding first ends to corresponding second ends. However, the ends of each seat may be arranged in any position (for example, at the center and the border of the testing device, spaced apart from them, any combination thereof and so on).

In an embodiment, each of the seats is slanted with respect to the resting surface with the second end closer to the resting surface than the first end. However, the seats may be slanted in any way (for example, downwards or upwards moving inwards the testing device) and at any angle.

In an embodiment, the corresponding windows are spaced apart from the first ends of the seats. However, the windows may be at any distance from the corresponding ends of the seats.

Further embodiments provide additional advantageous features, which may however be omitted at all in a basic implementation.

Particularly, in an embodiment the longitudinal axes of the seats form an angle of 5-30° with the resting surface. However, the possibility is not excluded of having the seats forming a different angle with the resting surface.

In an embodiment, a distance of the corresponding windows from the first ends of the seats is 10-50% of a length of the seats. However, the possibility is not excluded of having the windows at different distance from these ends of the seats.

In an embodiment, the testing device has a lateral surface extending between the resting surface and the imaging surface. However, the lateral surface may be of any type (for example, continuous or discontinuous, perpendicular to the resting surface, inclined inwards/outwards the testing device and so on).

In an embodiment, the seats comprise corresponding blind holes extending inwards from the lateral surface. However, the possibility is not excluded of having the seats formed in another way (for example, by through-holes, recesses and so on).

In an embodiment, each of the seats comprises a first portion with a constant section. However, the first portion may be of any length and at any position (for example, internal or external).

In an embodiment, each of the seats comprises a second portion with a section decreasing moving inwards the testing device. However, the second portion may be of any length and at any position (according to the ones of the first portion); moreover, its section may decrease in any way (for example, regularly or non-regularly, at any rate up to become null, and so on).

In an embodiment, the corresponding window exposes at least part of the first portion. However, the window may expose any part of the first portion (up to completely).

In an embodiment, the windows have corresponding edges at the imaging surface that are chamfered. However, the chamfered edges may form any angle with the imaging surface.

In an embodiment, the testing device comprises one or more optically machine-readable positional markers at the imaging surface (for determining a position of the testing device). However, the positional markers may be in any number, of any type (for example, codes, signs and so on) and arranged at any position (for example, at the center, at the windows and/or at the peripheral of the testing device); the positional markers may be used in any way for determining the position of the testing device (for example, its location defined by one or more positional markers, its orientation defined by multiple positional markers and/or format of one or more positional markers, any combination thereof and so on). In any case, this feature may also be implemented independently, in a testing device with the seats that are not inclined with respect to the resting surface.

In an embodiment, the testing device has a point symmetry with respect to a central point. However, the testing device may have any shape with point symmetry (for example, octagonal, hexagonal, squared, circular and so on).

In an embodiment, the positional markers comprise a central positional marker corresponding to the central point. However, the central positional marker may be of any type (for example, at the center of the testing device, around it and so on).

In an embodiment, the positional markers comprise one or more window positional markers corresponding to the windows. However, the window positional markers may be of any type (for example, with each window between a pair of corresponding window positional markers, each window positional marker close to a corresponding window, and so on).

In an embodiment, the testing device comprises one or more optically machine-readable informative markers at the imaging surface encoding device information relating to the testing device. However, the informative markers may be in any number and of any type (for example, incorporated in the positional markers and/or separated therefrom); the informative markers may encode any device information (for example, device identifier of the testing device, container identifiers for the seats, usage rules of the testing device, proof of authenticity of the testing device, type of containers for the seats and so on); the device information may be provided in any way (for example, QR codes, ArUco codes, bar codes and so on).

In an embodiment, the device information comprises a device identifier of the testing device. However, the device identifier may be of any type (for example, a serial number, an encrypted code and so on); the device identifier may be provided by any informative markers (for example, a single informative marker, a combination of two or more of the informative markers, and so on).

In an embodiment, the device information comprises corresponding container identifiers of expected types of the containers to be accommodated in the seats. However, the container identifiers may indicate the types of containers in any way (for example, concentration of (pre-defined) luminescence substances, nature and/or concentration of (varying) luminescence substances, product number of the containers and so on); the container identifiers may be provided by any informative markers (for example, a single informative marker, a combination of two or more informative markers, a corresponding informative marker for each seat, either the same as or different from the informative markers providing the device identifier, and so on).

In an embodiment, the positional markers and/or the informative markers are arranged on corresponding bottom surfaces of recesses extending from the imaging surface.

However, the recesses may be of any type (for example, with or without chamfered edges), size and shape (for example, circular, squared and so on, either the same as or simply compatible with the ones of the markers) and depth; in any case, the possibility is not excluded of having more markers arranged in each recess, or even having the markers (or at least part of them) arranged flush with the imaging surface.

In an embodiment, the bottom surface is parallel to the resting surface. However, the possibility is not excluded of having the bottom surface inclined with respect to the resting surface.

In an embodiment, the recesses have corresponding edges at the imaging surface that are chamfered. However, the chamfered edges may form any angle with the imaging surface.

In an embodiment, the testing device comprises one or more locking elements for locking the testing device on the supporting surface. However, the locking elements may be in any number, arranged at any position and of any type (for example, at the resting surface, at the lateral surface and the like, for locking the testing device magnetically, mechanically, such as with springs, clips, screws, Velcro strips, suction cups, multi-use adhesives, and so on).

In an embodiment, the locking elements comprise corresponding magnetic elements arranged at the resting surface. However, the magnetic elements may be in any number and at any positions, and they may be used to generate any attraction force with the supporting surface (when made of ferromagnetic material).

In an embodiment, the imaging surface around the windows is inclined with respect to the resting surface. However, the imaging surface around the windows may form any angle with the resting surface (down to be parallel thereto).

In an embodiment, the testing device comprises one or more human-readable seat indicators corresponding to the seats. However, the seat indicators may be arranged in any position (for example, on the imaging surface, on the lateral surface and so on).

In an embodiment, the seat indicators provide corresponding specifications of expected types of the containers to be accommodated in the seats. However, the seat indicators may specify the types of containers in any way (for example, with colors, names, codes and so on).

In an embodiment, the testing device comprises a testing light source at the imaging surface for generating a testing light corresponding to the luminescence light. However, the testing light source may be of any type and arranged at any position (for example, at the center or at the periphery of the testing device); the testing light may be of any type (for example, fixed or variable, such as via a wireless command transmitted by the luminescence imaging apparatus selecting the testing light in response to a manual command or according to predefined characteristics of the excitation light source of the luminescence imaging apparatus).

In an embodiment, the corresponding containers are accommodated in the seats in a non-removable way. However, the containers may be accommodated in the seats in any non-removable way (for example, fixed mechanically, glued, integral and so on).

In an embodiment, the corresponding containers are accommodated in the seats in a removable way. However, the containers may be accommodated in the seats in any removable way (for example, freely, snap fitted, with a selective blocking system and so on).

In an embodiment, the containers have corresponding end portions projecting from the seats. However, the end portions may be of any type (for example, caps, external ends of bottles/tubes and so on) and they may project from the seats at any extent (down to none).

In an embodiment, the end portions are with human-readable container indicators providing corresponding specifications of the containers. However, the container indicators may be of any type (either the same or different with respect to the seat indicators).

In an embodiment, the seat indicators are color-coded. However, the colors may be of any type and indicated in any way (for example, by their names, samples and so on).

In an embodiment, the container indicators are color-coded. However, the colors may be of any type and indicated in any way (for example, with the end portions themselves that are colored, with labels with their names, samples and so on).

In an embodiment, the containers comprise corresponding bottles containing the liquid and caps closing the bottles. However, the bottles and the caps may be of any type (for example, with the bottles shaped like vials or tubes, the caps that are screwed or press-fitted, and so on).

In an embodiment, the caps are colored according to the container indicators. However, the caps may be colored in any way (for example, completely, laterally, on the top and so on).

An embodiment provides a holder for use in the above-described testing device (comprising said resting surface, said seats for accommodating the containers and said windows). However, the holder may be put on the market as a stand-alone product (without the containers to be added later on).

An embodiment provides a method for testing a luminescence imaging apparatus with the above-mentioned testing device. However, the luminescence imaging apparatus may be of any type (see below) and it may be tested for any purpose and at any time (for example, for calibration after installation/maintenance, for verification before every use, for monitoring/comparison over time and so on); moreover, the method may be invoked in any way (for example, in response to any start command entered via any input unit of the fluorescence imaging apparatus, such as its keyboard, any pointing device, a dedicated button and the like, automatically, in any case with or without the possibility of entering information, such as the type of test or the change of the testing device, and so on).

In an embodiment, the method is performed with the testing device resting on the supporting surface within a field of view of an imaging head of the luminescence imaging apparatus. However, the imaging head may be of any type (see below) and the testing device may be placed within its field of view in any way (for example, by exploiting corresponding holding stations, freely, by moving either the testing device and/or the imaging head and so on).

In an embodiment, the method comprises the following steps under the control of a control unit of the luminescence imaging apparatus. However, the control unit may be of any type (see below).

In an embodiment, the method comprises acquiring (with a luminescence camera of the imaging head) a luminescence image of the field of view. However, the luminescence image may be of any type (for example, with any size, in colors or in black-and-white, in 2D or 3D, with any pixel/voxel values, such as RGB components, luminance components, in a single color or in corresponding different colors for multiple fluorescence agents, and so on) and it may be acquired with any luminescence camera (see below).

In an embodiment, the fluorescence image is representative of a luminescence light that is emitted by the luminescence substance of the containers in response to an excitation light thereof provided by an excitation light source of the imaging head. However, the excitation light may be of any type and it may be provided by any excitation light source (see below).

In an embodiment, the method comprises determining a representation of the windows in the luminescence image. However, the representation of the windows in the luminescence image may be determined in any way (for example, according to the position of the testing device in a corresponding photograph image, by searching them directly in the luminescence image and so on).

In an embodiment, the method comprises testing the luminescence imaging apparatus according to the representation of the windows in the luminescence image. However, this operation may be performed in any way (for example, by comparing the representation of each window with corresponding nominal values, with the representation of one or more other windows, with the representation of a background area, any combination thereof, in a single position or throughout the field of view, and so on).

Further embodiments provide additional advantageous features, which may however be omitted at all in a basic implementation.

Particularly, in an embodiment the method comprises acquiring (with a photograph camera of the imaging head) a photograph image of the field of view representative of a reflected light being reflected by the field of view. However, the photograph image may be of any type (either the same or different with respect to the luminescence image, such as in terms of size, colors/black-and-white, 2D/3D, pixel/voxel values and so on) and it may be acquired with any photograph camera (see below), either at the same time of or separately from the luminescence image.

In an embodiment, the method comprises retrieving a descriptor of the testing device. However, the descriptor may be retrieved in any way (for example, by reading locally, downloading remotely, and so on).

In an embodiment, the descriptor comprises an indication of a geometry of the testing device. However, the geometry of the testing device may be defined in any way only by the shape of the testing device (for example, when the shape allows determining both location and orientation of the testing device, such as having no point symmetry like with a projection/recess at a first one of the sites defining a sequence thereof), only by the positional markers (for example, in any number, of any type and arranged at any position allowing determining both location and orientation of the testing device as below), by characteristic points of the testing device (for example, its corners), by any combination thereof (for example, the shape of the testing device for determining the location and the positional markers for determining the orientation) and so on.

In an embodiment, the descriptor comprises an indication of a position of the windows in the testing device. However, the position of the windows in the testing device may be indicated in any way (for example, with respect to the positional markers, the holder and so on).

In an embodiment, the method comprises finding a position of the testing device in the photograph image according to the geometry of the testing device. However, the position of the testing device may be found in any way (for example, by applying any object recognition technique such as model-based, appearance-based, feature-based and the like, genetic algorithms and so on).

In an embodiment, the method comprises calculating a position of the windows in the photograph image according to the position of the testing device in the photograph image and the position of the windows in the testing device. However, the position of the windows in the photograph image may be calculated in any way (for example, by determining and then applying any transformation between real-word coordinates and image coordinates, such as of affine or non-rigid type, defined by a matrix, a transform, a vector and so on).

In an embodiment, the method comprises determining a representation of the windows in the luminescence image according to the position of the windows in the photograph image. However, the representation of the windows in the luminescence image may be determined in any way according to the position of the windows in the photograph image (for example, directly, by correcting possible misalignments between the two images, and so on).

In an embodiment, the method comprises retrieving the descriptor comprising a specification of the positional markers. However, the positional markers may be defined in any way (for example, by their position, orientation, format and so on).

In an embodiment, the method comprises retrieving the descriptor comprising an indication of a position of the windows with respect to the positional markers. However, the position of the windows with respect to the positional markers may be indicated in any way (for example, by their displacement, the coordinates of the positional markers and the coordinates of the windows in the testing device, and so on).

In an embodiment, the method comprises finding the position of the positional markers in the photograph image according to the specification of the positional markers. However, this operation may be performed in any way (see above).

In an embodiment, the method comprises calculating the position of the windows in the photograph image according to the position of the positional markers in the photograph image and the position of the windows with respect to the positional markers. However, this operation may be performed in any way (see above).

In an embodiment, the method comprises testing the luminescence imaging apparatus according to a comparison of the representation of each of the windows in the luminescence image with at least one nominal value. However, the nominal values may be in any number and of any type (for example, any statistical parameters, such as mean, variance, standard deviation, minimum/maximum values, median and so on); the test may be performed accordingly in any way (for example, by comparing the difference of each statistical parameter individually or a global difference with any threshold, and so on).

In an embodiment, the method comprises testing the luminescence imaging apparatus according to a comparison of the representation of each of the windows in the luminescence image with the representation of at least another one of the windows in the luminescence image. However, the representation of the windows may be compared in any way (for example, according to any statistical parameters of the windows as above, by comparing any relationship (such as ratio, difference and the like) with any threshold and so on).

In an embodiment, the method comprises determining a representation of a background area (different from the representations of the windows) in the luminescence image. However, the background area may be of any type (for example, corresponding to any positional marker or independent therefrom, and so on) and it may be determined in any way (for example, according to the position of the testing device and to the descriptor comprising an indication of a position of the background area in the testing device, by searching it directly and so on).

In an embodiment, the method comprises testing the luminescence imaging apparatus according to a comparison of the representation of each of the windows in the luminescence image with the representation of the background area in the luminescence image. However, this operation may be performed in any way (either the same or different with respect to the comparison with the other windows).

In an embodiment, the method comprises estimating corresponding expected types of the containers according to a comparison of the representations of the windows in the luminescence image with a plurality of pre-defined specifications of possible types of the containers. However, the expected types of the containers may be estimated in any way (for example, by selecting them together (as the closest combination) or individually (as the closest one) according to any criterion, and so on).

In an embodiment, the method comprises determining a representation of the informative markers in the photograph image. However, the informative markers may be determined in any way (for example, already given by the positional markers when coincident with them, according to the position of the testing device and to the descriptor comprising an indication of a position of the informative markers in the testing device, by searching them directly and so on).

In an embodiment, the method comprises determining the device information according to the representation of the informative markers. However, the device information may be determined in any way (for example, extracted from the informative markers directly, retrieved according thereto either locally or remotely, and so on).

In an embodiment, the method comprises testing the luminescence imaging apparatus according to the device information. However, the device information may be used in any way (for example, to determine expected type of containers, to retrieve usage rules, to retrieve usage information and so on).

In an embodiment, the method comprises determining corresponding expected types of the containers according to the device information. However, the type of the containers may be determined in any way (for example, directly from the device information, retrieved according thereto either locally or remotely, such as via corresponding container identifiers, and so on).

In an embodiment, the method comprises testing the luminescence imaging apparatus according to pre-defined specifications of the expected types of the containers. However, the specifications of the types of containers may be of any type (for example, nominal values of any number and type of corresponding statistical parameters) and they may be retrieved in any way (for example, locally or remotely); moreover, the test may be performed accordingly in any way (for example, by comparing the difference of each statistical parameter individually or any global difference with any threshold, and so on).

In an embodiment, the method comprises determining a representation of the end portions of the containers in the photograph image. However, the end portions may be determined in any way (for example, according to the position of the testing device and to the descriptor comprising an indication of a position of the end portions in the testing device, by searching them directly and so on).

In an embodiment, the method comprises verifying a configuration of the testing device according to a matching of the representation of the end portions in the photograph image with pre-defined definitions of the corresponding expected types of the containers. However, the definitions of the types of containers may be of any type (for example, color definitions given by any number and type of statistical parameters, color names and so on) and they may be retrieved in any way (for example, locally or remotely); the verification of the configuration of the testing device may be performed accordingly in any way (for example, by comparing the difference of each statistical parameter individually or a global difference with any threshold, by comparing the names, with or without the further verification of the seat indicators, and so on).

In an embodiment, the method comprises finding a position of the testing device in the luminescence image. However, the position of the testing device may be found in the luminescence image in any way (either the same or different with respect to the photograph image).

In an embodiment, the method comprises testing the luminescence imaging apparatus according to an alignment between the photograph image and the luminescence image determined according to the position of the testing device in the photograph image and the position of the testing device in the luminescence image. However, this operation may be performed in any way (for example, by comparing the distance between each pair of corresponding markers individually, any global value based on the distances between all the pairs of corresponding markers, a distance between the holders and the like with any threshold, and so on).

In an embodiment, the method comprises retrieving one or more usage rules of the testing device. However, the usage rules may be in any number and of any type (for example, maximum usage in terms of length of tests or number of tests, down to a single one when the testing device is disposable, elapsed time from a production date, expiration date and so on), and they may be retrieved in any way (for example, by reading locally, downloading remotely, indiscriminately or according to the device identifier, and so on).

In an embodiment, the method comprises enabling said testing the luminescence imaging apparatus according to the usage rules. However, the test may be enabled according to the usage rules in any way (for example, by verifying the usage rules in any way, such as requiring compliance with all or only part of them, by enabling the test in any way according to the corresponding result, such as preventing it, simply warning the operator, notifying the service provider, any combination thereof, and so on).

In an embodiment, the method comprises retrieving usage information of one or more previous executions of said testing the luminescence imaging apparatus. However, the usage information may be of any type (for example, length of tests, number of tests, date of last test and so on) and it may be retrieved in any way (for example, locally or remotely, and so on).

In an embodiment, the method comprises enabling said testing the luminescence imaging apparatus according to the usage information. However, the test may be enabled according to the usage information in any way (for example, by verifying it against any usage rules as above, with the usage rules that may be pre-defined locally or remotely, retrieved according to the device identifier, and by enabling the test in any way according to the corresponding result as above, and so on).

In an embodiment, the method comprises saving the usage information of said testing the luminescence imaging apparatus. However, the usage information may be saved in any way (for example, individually or incrementally, locally or remotely, and so on).

In an embodiment, the method comprises retrieving the usage rules and/or the usage information according to the device information. However, the usage rules and the usage information may be retrieved in any way (for example, extracted directly from the device information, determined according thereto either locally or remotely, such as via a corresponding device identifier, and so on).

In an embodiment, the method comprises acquiring a further luminescence image of the field of view (with the luminescence camera) while the excitation light source of the imaging head is turned off and the testing light source is turned on. However, the further luminesce image may be acquired at any time (either before or after the luminesce image).

In an embodiment, the method comprises testing an acquisition unit of the imaging head (for acquiring the luminescence images) according to the further luminescence image and predefined characteristics of the testing light source. However, the acquisition unit may be of any type (see below); the characteristics of the testing light source may be of any type (for example, nominal values of any number and type of statistical parameters) and they may be retrieved in any way (for example, locally or remotely); moreover, the test may be performed accordingly in any way (for example, by comparing the difference of each statistical parameter individually or a global difference with any threshold, and so on).

In an embodiment, the method comprises testing an illumination unit of the imaging head (for generating the excitation light) according to a result of said testing the luminescence imaging apparatus and a result of said testing the acquisition unit. However, the illumination unit may be of any type (see below) and it may be tested in any way (for example, by conditioning the representation of the windows according to the test of the acquisition unit and then repeating the test of the whole luminescence imaging apparatus, by extrapolating it from the previous test of the whole luminescence imaging apparatus according to the test of the acquisition unit, and so on).

In an embodiment, the method comprises determining a displacement of the testing device and/or the imaging head from a target position according to the position of the testing device in the photograph image. However, the displacement may be determined in any way (for example, for each coordinate or globally, and so on) from the position of the testing device defined in any way (for example, by the holder and/or the positional markers) to any target position thereof (for example, retrieved locally or remotely, inserted manually and so on); moreover, the displacement may be defined for the testing device alone, the imaging head alone or both of them.

In an embodiment, the method comprises outputting an indication of a movement of the testing device and/or the imaging head for reaching the target position according to the displacement thereof on an output unit of the luminescence imaging apparatus. However, the movement may be of any type (for example, translation and/or rotation in plane or space for the testing device alone, the imaging head alone or both of them, and so on); moreover, the indication of the movement may be output in any way (for example, displayed, uttered and so on) on any output unit (for example, monitor, loudspeaker and so on). This feature may be used for any purpose (for example, to arrange the testing device correctly, to test the fluorescence imaging apparatus throughout the field of view and so on).

In an embodiment, the method comprises outputting an indication of a result of said testing the luminescence imaging apparatus on an output unit of the luminescence imaging apparatus. However, the result may be of any type (for example, simply passed/failed or with more or less details about every verification); moreover, the result may be output in any way (for example, displayed, printed and so on) on any output unit (for example, monitor, printer and so on) and for any purpose (for example, for enabling a corresponding imaging process, requesting a maintenance of the luminescence imaging apparatus either manually or automatically, such as by message, e-mail and the like, and so on).

In an embodiment, the method comprises transmitting an indication of a result of said testing the luminescence imaging apparatus to a remote computing system over a telecommunication network. However, the result may be of any type (either the same or different with respect to above) and it may be transmitted to any remote computing system in any way (for example, by uploading it, via e-mail and so on) over any network (for example, the Internet, a LAN and so on).

In an embodiment, the method comprises repeating the following loop in a non-operative condition of the luminescence imaging apparatus. However, the loop may be repeated with any frequency in any non-operative condition (for example, when no imaging process is in progress as indicated by corresponding start and stop commands entered by the operator via any input unit, in stand-by and so on).

In an embodiment, the loop comprises acquiring a further photograph image of the field of view with the photograph camera. However, the further photograph image may be of any type (either the same or different with respect to the photograph image) and it may be acquired in any way (for example, alone or with a corresponding fluorescence image to be used for the test after exiting the loop, and so on).

In an embodiment, the loop comprises searching a representation of the testing device in the further photograph image according to the geometry of the testing device. However, the testing device may be searched in any way according to its descriptor (either the same or different with respect to above for determining its position).

In an embodiment, the loop is performed until the representation of the testing device in the further photograph image has been found. However, the exit condition of the loop may be defined in any way (for example, according to a match of the shape of the testing device, a match of the positional markers, both of them, and so on).

In an embodiment, the method comprises triggering said testing the luminescence imaging apparatus in response to the representation of the testing device in the further photograph image being found. However, the test may be trigged in any way (for example, automatically or requiring a manual confirmation, with or without prompting the operator to enter information, and so on).

Generally, similar considerations apply if the same solution is implemented with an equivalent method (by using similar steps with the same functions of more steps or portions thereof, removing some non-essential steps or adding further optional steps); moreover, the steps may be performed in a different order, concurrently or in an interleaved way (at least in part).

An embodiment provides a computer program that is configured for causing a control unit of a luminescence imaging apparatus to perform the above-mentioned method when the computer program is executed on the control unit. An embodiment provides a computer program product comprising a computer readable storage medium embodying a computer program, the computer program being loadable into a working memory of a control unit of a luminescence imaging apparatus thereby configuring the control unit to perform the same method. However, the software program may be implemented as a stand-alone module, as a plug-in for a pre-existing software program (for example, the imaging manager), or even directly in the latter. In any case, similar considerations apply if the software program is structured in a different way, or if additional modules or functions are provided; likewise, the memory structures may be of other types, or may be replaced with equivalent entities (not necessarily consisting of physical storage media). The program may take any form suitable to be used by any control unit (see below), thereby configuring the control unit to perform the desired operations; particularly, the program may be in the form of external or resident software, firmware or microcode (either in object code or in source code, for example, to be compiled or interpreted). Moreover, it is possible to provide the program on any computer readable storage medium. The storage medium is any tangible medium (different from transitory signals per se) that may retain and store instructions for use by the control unit. For example, the storage medium may be of the electronic, magnetic, optical, electromagnetic, infrared, or semiconductor type; examples of such storage medium are fixed disks (where the program may be pre-loaded), removable disks, memory keys (for example, of USB type), and the like. The program may be downloaded to the control unit from the storage medium or via a network (for example, the Internet, a wide area network and/or a local area network comprising transmission cables, optical fibers, wireless connections, network devices); one or more network adapters in the control unit receive the program from the network and forward it for storage into one or more storage devices of the control unit. In any case, the solution according to an embodiment of the present disclosure lends itself to be implemented even with a hardware structure (for example, by electronic circuits integrated in one or more chips of semiconductor material), or with a combination of software and hardware suitably programmed or otherwise configured.

An embodiment provides a luminescence imaging apparatus comprising a control unit for performing each step of the above-mentioned method. However, the luminescence imaging apparatus may be of any type (for example, a medical equipment, an industrial equipment and the like, for use in any luminescence applications, such as fluorescence applications in diagnostics, therapy or surgery, and so on); the luminescence imaging apparatus may comprise any control unit (for example, any integrated central unit, any separate computer, such as an industrial PC, and so on), any illumination unit (for example, based on laser, LEDs, UV/halogen/Xenon lamp, and so on), any acquisition unit (for example, based on any number and type of lenses, wave guides, mirrors, CCD, ICCD, EMCCD, CMOS, InGaAs or PMT sensors, and so on), any imaging head (for example, mounted on articulated arm, pivoting arm, stand-alone with wireless connection, hand-held and so on) and any output device (for example, monitor, printer, network connection, head-mounted projector, and so on).

Further embodiments provide additional advantageous features, which may however be omitted at all in a basic implementation.

Particularly, in an embodiment the luminescence imaging apparatus comprises a supporting surface for resting the testing device. However, the supporting surface may be of any type (for example, a top surface of any trolley, a cantilever, either fixed or hidden, and so on).

In an embodiment, the luminescence imaging apparatus comprises a holding station for holding the testing device in an imaging position on the supporting surface in a removable way. However, the holding station may be of any type (for example, a recess, a socket and so on) for holding the testing device in any removable way (for example, freely, snap fitted, with a selective blocking system and so on).

In an embodiment, the luminescence imaging apparatus comprises a further holding station for holding the imaging head in an acquisition position in a removable manner. However, the further holding station may be of any type (for example, a ring, a hook and so on, either separate or combined with the holding station) for holding the imaging head in any removable way (for example, freely, snap fitted, with a selective blocking system and so on).

In an embodiment, the testing device in the imaging position falls within the field of view of the imaging head in the acquisition position. However, the testing device may fall within the field of view in any way (for example, in a fixed or variable way in one or more dimensions, and so on).

In an embodiment, a center of the testing device in the imaging position is on an optical axis of the imaging head in the acquisition position. However, the possibility of having the testing device in one or more different positions is not excluded.

An embodiment provides a luminescence imaging system comprising the above-mentioned luminescence imaging apparatus and testing device (for testing the luminescence imaging apparatus). However, the testing device may be put on the market as a stand-alone product for use with any pre-existing luminescence imaging apparatus.

Generally, similar considerations apply if the testing device, the luminescence imaging apparatus and the luminescence imaging system each has a different structure or comprises equivalent components or it has other operative characteristics. In any case, every component thereof may be separated into more elements, or two or more components may be combined together into a single element; moreover, each component may be replicated to support the execution of the corresponding operations in parallel. Moreover, unless specified otherwise, any interaction between different components generally does not need to be continuous, and it may be either direct or indirect through one or more intermediaries.

What is claimed is:

1. A testing device for testing a luminescence imaging apparatus, wherein the testing device comprises:
   a resting surface for resting the testing device on a supporting surface,
   one or more seats,
   one or more containers each filled with a liquid comprising at least one luminescence substance, each of the containers being accommodated in a corresponding one of the seats, and
   one or more windows corresponding to the seats being opened in an imaging surface of the testing device opposite the resting surface, each of the windows exposing a part of the corresponding seat for imaging the luminescence substance of a corresponding part of the container accommodated therein being transparent to an excitation light of the luminescence substance and to a luminescence light emitted by the luminescence substance when illuminated by the excitation light, wherein the seats extend along corresponding longitudinal axes from corresponding first ends to corresponding second ends, each of the seats being slanted with respect to the resting surface with the second end closer to the resting surface than the first end, the longitudinal axes of the seats form an angle of 5-30° with the resting surface, and the corresponding windows are spaced apart from the first ends of the seats.

2. The testing device according to claim 1, wherein a distance of the corresponding windows from the first ends of the seats is 10-50% of a length of the seats.

3. The testing device according to claim 1, wherein the testing device has a lateral surface extending between the resting surface and the imaging surface, the seats comprising corresponding blind holes extending inwards from the lateral surface.

4. The testing device according to claim 1, wherein each of the seats comprises a first portion with a constant section and a second portion with a section decreasing moving inwards the testing device, the corresponding window exposing at least part of the first portion.

5. The testing device according to claim 1, wherein the windows have corresponding edges at the imaging surface being chamfered.

6. The testing device according to claim 1, wherein the testing device comprises one or more optically machine-readable positional markers at the imaging surface for determining a position of the testing device.

7. The testing device according to claim 6, wherein the testing device has a point symmetry with respect to a central point, the positional markers comprising a central positional marker corresponding to the central point.

8. The testing device according to claim 7, wherein the testing device comprises one or more window positional markers corresponding to the windows.

9. The testing device according to claim 6, wherein the positional markers and/or the informative markers are arranged on corresponding bottom surfaces of recesses extending from the imaging surface, the bottom surfaces being parallel to the resting surface.

10. The testing device according to claim 9, wherein the recesses have corresponding edges at the imaging surface being chamfered.

11. The testing device according to claim 1, wherein the testing device comprises one or more optically machine-readable informative markers at the imaging surface encoding device information relating to the testing device.

12. The testing device according to claim 11, wherein the device information comprises a device identifier of the testing device.

13. The testing device according to claim 11, wherein the device information comprises corresponding container identifiers of expected types of the containers to be accommodated in the seats.

14. The testing device according to claim 1, wherein the testing device comprises one or more locking elements for locking the testing device on the supporting surface.

15. The testing device according to claim 14, wherein the locking elements comprise corresponding magnetic elements arranged at the resting surface.

16. The testing device according to claim 1, wherein the imaging surface around the windows is inclined with respect to the resting surface.

17. The testing device according to claim 1, wherein the testing device comprises one or more human-readable seat indicators corresponding to the seats, the seat indicators providing corresponding specifications of expected types of the containers to be accommodated in the seats.

18. The testing device according to claim 17, wherein the seat indicators are color-coded.

19. The testing device according to claim 1, wherein the testing device comprises a testing light source at the imaging surface for generating a testing light corresponding to the luminescence light.

20. The testing device according to claim 1, wherein the corresponding containers are accommodated in the seats in a non-removable way.

21. The testing device according to claim 1, wherein the corresponding containers are accommodated in the seats in a removable way.

22. The testing device according to claim 1, wherein the containers have corresponding end portions projecting from the corresponding seats with human-readable container indicators providing corresponding specifications of the containers.

23. The testing device according to claim 22, wherein the container indicators are color-coded.

24. The testing device according to claim 22, wherein the containers comprise corresponding bottles containing the liquid and caps closing the bottles, the caps being colored according to the container indicators.

25. A holder for use in the testing device according to claim 1, wherein the holder comprises said resting surface, said seats for accommodating the containers and said windows.

26. A luminescence imaging system comprising a luminescence imaging apparatus and a testing device for testing the luminescence imaging apparatus, wherein the testing device comprises:
a resting surface for resting the testing device on a supporting surface,
one or more seats,
one or more containers each filled with a liquid comprising at least one luminescence substance, each of the containers being accommodated in a corresponding one of the seats,
one or more windows corresponding to the seats being opened in an imaging surface of the testing device opposite the resting surface, each of the windows exposing a part of the corresponding seat for imaging the luminescence substance of a corresponding part of the container accommodated therein being transparent to an excitation light of the luminescence substance and to a luminescence light emitted by the luminescence substance when illuminated by the excitation light, and
wherein the seats extend along corresponding longitudinal axes from corresponding first ends to corresponding second ends, each of the seats being slanted with respect to the resting surface with the second end closer to the resting surface than the first end, the longitudinal axes of the seats form an angle of 5-30° with the resting surface, and the corresponding windows are spaced apart from the first ends of the seats.

* * * * *